United States Patent
Klotsman et al.

(10) Patent No.: US 11,633,378 B2
(45) Date of Patent: *Apr. 25, 2023

(54) METHODS AND COMPOSITIONS FOR DELIVERING MYCOPHENOLIC ACID ACTIVE AGENTS TO NON-HUMAN MAMMALS

(71) Applicant: OKAVA PHARMACEUTICALS, INC., San Francisco, CA (US)

(72) Inventors: Michael Klotsman, San Francisco, CA (US); Padmaja Shivanand, Seattle, WA (US); Wayne H. Anderson, Raleigh, NC (US); Gayatri Sathyan, Karnataka (IN)

(73) Assignee: Okava Pharmaceuticals, Inc., San Francisco, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 16/493,708

(22) PCT Filed: Mar. 13, 2018

(86) PCT No.: PCT/US2018/022266
§ 371 (c)(1),
(2) Date: Sep. 12, 2019

(87) PCT Pub. No.: WO2018/170022
PCT Pub. Date: Sep. 20, 2018

(65) Prior Publication Data
US 2020/0030285 A1    Jan. 30, 2020

Related U.S. Application Data

(60) Provisional application No. 62/470,806, filed on Mar. 13, 2017, provisional application No. 62/503,270, filed on May 8, 2017.

(51) Int. Cl.
| | | |
|---|---|---|
| *A61K 9/50* | (2006.01) | |
| *A61K 31/365* | (2006.01) | |
| *A61K 31/343* | (2006.01) | |
| *A61K 9/20* | (2006.01) | |
| *A61P 37/06* | (2006.01) | |
| *A61P 37/02* | (2006.01) | |
| *A61K 9/16* | (2006.01) | |
| *A61K 9/48* | (2006.01) | |

(52) U.S. Cl.
CPC ............ *A61K 31/365* (2013.01); *A61K 9/167* (2013.01); *A61K 9/2072* (2013.01); *A61K 9/5078* (2013.01); *A61K 31/343* (2013.01); *A61P 37/02* (2018.01); *A61P 37/06* (2018.01); *A61K 9/2027* (2013.01); *A61K 9/2054* (2013.01); *A61K 9/4808* (2013.01)

(58) Field of Classification Search
None
See application file for complete search history.

(56) References Cited

U.S. PATENT DOCUMENTS

| | | |
|---|---|---|
| 4,808,413 A | 2/1989 | Joshi et al. |
| 5,049,394 A | 9/1991 | Howard et al. |
| 6,306,900 B1 | 10/2001 | Haeberlin et al. |
| 2004/0127403 A1* | 7/2004 | Parenti ................... A61K 38/13 514/192 |
| 2007/0036857 A1* | 2/2007 | Becker ................. A61K 9/2846 424/470 |
| 2008/0206322 A1 | 8/2008 | Becker et al. |
| 2010/0056493 A1 | 3/2010 | Jain et al. |
| 2011/0008426 A1 | 1/2011 | Jain et al. |
| 2011/0086102 A1 | 4/2011 | Silver et al. |
| 2011/0223249 A1 | 9/2011 | Jain et al. |

FOREIGN PATENT DOCUMENTS

| | | | |
|---|---|---|---|
| CN | 1994295 A | 7/2007 | |
| CN | 101010070 A | 8/2007 | |
| CN | 102793658 A | 11/2012 | |
| CN | 103845323 A | 6/2014 | |
| GB | 1203328 A * | 8/1970 | ............. A61K 31/52 |
| KR | 10-2011-0091252 A | 8/2011 | |
| WO | 2006/024479 A2 | 3/2006 | |
| WO | 2018/170022 A2 | 9/2018 | |

OTHER PUBLICATIONS

Arns et al., "Enteric-coated mycophenolate sodium delivers bioequivalent MPA exposure compared with mycophenolate mofetil," *Clin. Transplant* 19: 199-206, 2005.

Arns, "Noninfectious Gastrointestinal (GI) Complications of Mycophenolic Acid Therapy: A Consequence of Local GI Toxicity?" *Transplantation Proceedings* 39: 88-93, 2007.

Chanda et al., "Comparative Gastrointestinal Effects of Mycophenolate Mofetil Capsules and Enteric-Coated Tablets of Sodium-Mycophenolic Acid in Beagle Dogs," *Transplantation Proceedings* 34: 3387-3392, 2002.

Chandira et al., "Development and Evaluation of Delayed-Release Tablets of Mycophenolate Sodium," *The Pharma Innovation—Journal* 2(2): 59-67, 2013.

Guzera et al., "In Vitro Influence of Mycophenolic Acid on Selected Parameters of Stimulated Peripheral Canine Lymphocytes," *PLoS ONE* 11(5):e0154429, 2016, (20 pages).

Kamba et al., "Evaluation of the mechanical destructive force in the stomach of dog," *International Journal of Pharmaceutics* 228: 209-217, 2001.

(Continued)

*Primary Examiner* — Susan T Tran
(74) *Attorney, Agent, or Firm* — Seed Intellectual Property Law Group LLP

(57) ABSTRACT

The present disclosure provides methods and compositions for modified delivery of mycophenolic acid active agents, including sodium mycophenolate, in veterinary subjects. Presently disclosed methods and compositions are useful, for example, to treat autoimmune diseases, blood disorders associated with IMPDH activity, and immune rejection related to transplant or graft procedures.

12 Claims, 15 Drawing Sheets

(56) References Cited

OTHER PUBLICATIONS

Missaghi et al., "Investigation of Venlafaxine HC1 Release from Extruded and Spheronized Beads Coated with Ethylcellulose using Organic or Aqueous Coating Systems," *Controlled Release Society Annual Meeting*, Jul. 2008 (3 pages).

Shipkova et al., "Determination of the Acyl Glucuronide Metabolite of Mycophenolic Acid in Human Plasma by HPLC and Emit," *Clinical Chemistry* 46(3): 365-372, 2000.

Soares et al., "Novel application of Ki67 to quantify antigen-specific in vitro lymphoproliferation," *Journal of Immunological Methods* 362:43-50, 2010.

Winnicki et al., "An inosine 5'-monophosphate dehydrogenase 2 single-nucleotide polymorphism impairs the effect of mycophenolic acid," *The Pharmacogenomics Journal* 10: 70-76, 2010.

International Search Report and Written Opinion, dated Oct. 10, 2018, for International Patent Application No. PCT/US2018/022266, 15 pages.

International Search Report and Written Opinion, dated Jun. 21, 2019, for International Patent Application No. PCT/US2018/050079, 16 pages.

Sandeep et al., "An overview on multiparticulate drug delivery system: Pellets," *Int. J. of Pharmacy and Analytical Research* 4(3):264-275, 2015.

Kohno et al., "Treatment of rheumatic diseases: current status and future prospective. Topics: II. Immunosuppressant/antirheumatic drugs; 9. Mycophenolate mofetil," *Journal of the Japanese Society of Internal Medicine* 100(10):2954-2959, 2011, (with English abstract).

Cellcept Capsule 250, pharmaceutical interview form, revised 17th edition, 2013.

\* cited by examiner

METHODS AND COMPOSITIONS FOR DELIVERING MYCOPHENOLIC ACID ACTIVE AGENTS TO NON-HUMAN MAMMALS

BACKGROUND

Technical Field

Autoimmune diseases represent a heterogeneous family of chronic diseases. The hallmarks of such diseases include proliferation of lymphocytes, development of autoantibodies, and dysregulation of the immune system leading to chronic inflammation and tissue damage. In the veterinary context, autoimmune diseases represent a category of diseases with few viable treatment options.

Description of the Related Art

Mycophenolate mofetil has been recognized as a treatment for autoimmune diseases and other conditions in both human and veterinary subjects. However, current methods and compositions for delivery of mycophenolate mofetil and sodium mycophenolate can produce significant side effects in veterinary subjects, including, for example, gastrointestinal intolerance related to mucosal ulceration, and erosion and necrosis of the stomach and the small and large intestines. See, e.g., Arns, W., "Noninfectious Gastrointestinal (GI) Complications of Mycophenolic Acid Therapy: A Consequence of Local GI Toxicity?," Transplantation Proceedings 39:88-93 (2007).

BRIEF SUMMARY

The present disclosure provides methods for delivering an MPA active agent in a veterinary subject, comprising delivering, via oral administration, a mycophenolic acid (MPA) active agent to a lower gastrointestinal tract of the veterinary subject in a modified release profile.

In some embodiments, a method comprises administering a modified-release veterinary composition to a veterinary subject in an amount effective to provide for a modified MPA release profile in a veterinary subject relative to an immediate-release MPA formulation administered to a reference veterinary subject. In further embodiments, presently disclosed methods and compositions provide for a MPA release profile having one or more desired PK characteristic, such as, e.g., a desired [MPA] $C_{max}$, a plasma [MPA] level that is maintained at, above, or below a certain threshold for a desired period of time, or a release rate that is more consistent over time as compared to a release rate of an immediate-release formulation, or the like.

For example, in some embodiments, following the administration, the veterinary subject has a plasma [MPA] $C_{max}$ that is lower than a plasma [MPA] $C_{max}$ from a veterinary subject administered a reference immediate-release MPA formulation. In particular embodiments, a method comprises administering to a veterinary subject a modified-release composition of the present disclosure, whereupon following the administration, the veterinary subject has a plasma [MPA] $C_{max}$ of less than about 2500 ng/nL, less than about 2000 ng/mL, or less than about 1500 ng/mL. In certain such embodiments of the methods, a veterinary subject is administered a modified-release composition of the present disclosure and, following the administration, maintains a plasma [MPA] of more than about 500 ng/mL for at least about 3 hours, at least about 4 hours, or at least about 5 hours following $T_{max}$.

Also provided herein are methods that comprise administering to a veterinary subject a modified-release composition, whereupon following the administration, the veterinary subject has a [MPA] AUC over a period of time that is increased by at least about 1.5×, at least about 2×, at least about 2.5×, at least about 3×, at least about 4×, at least about 5×, at least about 10×, or more as compared to the [MPA] AUC of a reference veterinary subject administered an immediate-release formulation, over the same period of time.

Presently disclosed methods and compositions are, in certain embodiments, also useful for providing a desired drug:metabolite (i.e., MPA:metabolite) ratio. For example, in particular embodiments, the metabolite comprises MPAG and a MPA:MPAG ratio is from about 1:1 to about 10:1. In further embodiments, a MPA:MPAG ratio is from about 1.5:1 to about 5:1. In still further embodiments, a MPA:MPAG ratio is about 2:1. In other embodiments, a metabolite comprises AcMPAG and a MPA:AcMPAG ratio is from about 50:1 to about 250:1, or from about 100:1 to about 200:1. In some such embodiments, a MPA:AcMPAG ratio is about 150:1.

In some embodiments, following an oral administration, a veterinary subject has a MPA:metabolite ratio that is elevated as compared to a corresponding MPA:metabolite ratio obtained from a reference veterinary subject following administration of an immediate-release reference oral dosage of mycophenolate mofetil (MMF) thereto.

Also provided herein are methods for delivering a WA active agent in a veterinary subject, comprising delivering, via oral administration, a WA active agent to a lower gastrointestinal tract of the veterinary subject in a modified release such that following the administration, a $C_{max}$ plasma [MPA] from about 1 µg/mL to about 10 µg/mL is achieved in the veterinary subject.

Also provided herein are methods for delivering a WA active agent in a veterinary subject, comprising delivering, via oral administration, a WA active agent to a lower gastrointestinal tract of the veterinary subject in a modified release such that following the administration, a $C_{max}$ plasma [MPA] of about 1 µg/mL to about 10 µg/mL for about 4 to about 24 hours is achieved in the veterinary subject.

Also provided herein are methods for delivering a WA active agent in a veterinary subject, comprising delivering, via oral administration, a WA active agent to a lower gastrointestinal tract of the veterinary subject in a modified release such that following the administration, a $C_{max}$ plasma [MPA] of from about 3 µg/mL to about 5 µg/mL for about 8 to about 24 hours is achieved in the veterinary subject.

Also provided herein are methods for delivering a WA active agent in a veterinary subject, comprising delivering, via oral administration, a WA active agent to a lower gastrointestinal tract of the veterinary subject in a modified release such that following the administration, a $C_{max}$ plasma [MPA] of from about 5 to about 6 µg/mL is achieved in the veterinary subject and from about 2.5 µg/mL/h to about 5 µg/mL of the MPA active agent is released in the veterinary subject for about 4 to about 10 hours.

Also provided herein are methods for delivering a WA active agent in a veterinary subject, comprising delivering, via oral administration, a WA active agent to a lower gastrointestinal tract of the veterinary subject in a modified release such that following the administration, a $C_{max}$ plasma [MPA] in the veterinary subject of about 6 µg/mL is achieved.

Also provided herein are modified-release veterinary compositions, comprising:
a core having a diameter of less than about 10 mm;
an active layer disposed over at least a portion of the core and comprising a MPA active agent;
an optional seal coat disposed over the active layer; and,
a modified-release layer disposed over the seal coat layer and comprising from about 5 wt % to about 50 wt % of the composition,
wherein the MPA active agent is from about 20 wt % to about 90 wt % of the composition and the modified-release layer is from about 5 wt % to about 50 wt % of the composition, and whereupon following administration of the composition to a veterinary subject, a MPA:metabolite ratio is elevated in the veterinary subject as compared to a corresponding MPA:metabolite ratio obtained from a reference veterinary subject following administration of a immediate-release reference oral dosage of MMF.

Also provided are modified-release veterinary compositions, comprising:
an extruded core having a diameter of less than about 10 mm;
a MPA active agent disposed at least partially within the core;
a optional seal coat disposed over the MPA active agent and the core; and,
a modified-release layer disposed over the seal coat layer,
wherein the MPA active agent is from about 20 wt % to about 90 wt % of the composition and the modified-release layer is from about 5 wt % to about 50 wt % of the composition, and whereupon following administration of the composition to a veterinary subject, a MPA:metabolite ratio is elevated as compared to a corresponding MPA:metabolite ratio obtained from a reference veterinary subject following administration of an immediate-release oral dosage of MMF.

In certain embodiments, a MPA:metabolite ratio obtained following administration of a presently disclosed modified-release composition to a veterinary subject is a ratio of MPA:MPAG.

In further embodiments, the MPA:MPAG ratio obtained following administration of a presently disclosed modified-release composition to a veterinary subject is at least about 1.5 fold-higher as compared to a MPA:MPAG ratio obtained following administration of a reference immediate-release oral dosage of MW to the reference veterinary subject.

In certain embodiments, a MPA:metabolite ratio obtained using a presently disclosed modified-release composition is a ratio of MPA:AcMPAG.

Also provided are methods of immunosuppressing a veterinary subject in need thereof, wherein the methods comprise orally administering to the subject an effective amount of a modified-release veterinary composition according to the present disclosure.

Also provided are methods for inhibiting inosine monophosphate dehydrogenase (IMPDH) activity in a veterinary subject, wherein the methods comprise orally administering to the veterinary subject an effective amount of a modified-release veterinary composition according to the present disclosure.

In certain embodiments of the methods, administration of an effective amount of a modified release veterinary composition according to any of the embodiments described herein inhibits IMPDH activity by at least about 10%, at least about 20%, at least about 30%, at least about 40%, at least about 50%, at least about 60%, at least about 70%, at least about 80%, or more.

The present disclosure also provides methods for reducing lymphocyte count and/or activity in a veterinary subject in need thereof, wherein the methods comprise orally administering to the subject an effective amount of a modified-release veterinary composition according to the present disclosure.

Also provided herein are methods for modulating an inflammatory response in a veterinary subject, wherein the methods comprise orally administering to the subject an effective amount of a modified-release veterinary composition according to the present disclosure.

The present disclosure also provides methods of preferentially delivering a WA active agent through a lower GI tract of a veterinary subject, wherein the methods comprise orally administering to the subject a modified-release veterinary composition according to the present disclosure.

Also provided herein are methods for reducing the exposure of a veterinary subject to an inactive MPA metabolite in a WA therapy, wherein the methods comprise orally administering to the subject a modified-release veterinary composition according to the present disclosure.

Methods for reducing the exposure of a veterinary subject to a MPA metabolite that is associated with an adverse effect are also provided herein, wherein the methods comprise orally administering to the subject a modified-release veterinary composition according to the present disclosure.

Further aspects, embodiments, features, and advantages of the disclosure, as well as the structure and operation of the certain embodiments, are described in detail below with reference to accompanying drawings.

DETAILED DESCRIPTION

Figure 1:
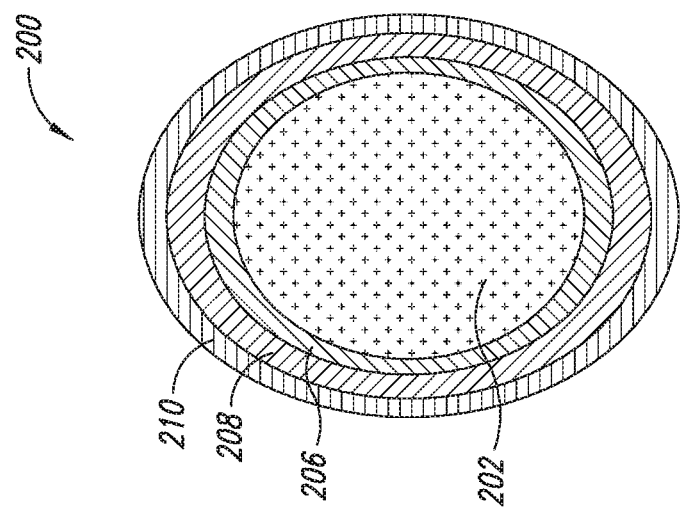
FIG. 1 shows a representation of an embodiment of a modified-release veterinary composition in accordance with an embodiment hereof.

The present disclosure provides methods and compositions for modified delivery of mycophenolic acid active agents, including sodium mycophenolate, in veterinary subjects. The methods and compositions disclosed herein are useful for, among other applications, treating autoimmune diseases, blood disorders associated with IMPDH activity, and immune rejection related to transplant or graft procedures.

The published patents, patent applications, websites, company names, and scientific literature referred to herein are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of this specification.

Definitions

Prior to setting forth this disclosure in more detail, it may be helpful to an understanding thereof to provide definitions of certain terms to be used herein. Additional definitions are set forth throughout this disclosure.

Technical and scientific terms used herein have the meaning commonly understood by one of skill in the art to which the present application pertains, unless otherwise defined. Reference is made herein to various methodologies and materials known to those of ordinary skill in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

"Optional" or "optionally" means that the subsequently described element, component, event, or circumstance may or may not occur, and that the description includes instances in which the element, component, event, or circumstance occurs and instances in which they do not.

The term "consisting essentially of" is not equivalent to "comprising" and refers to the specified materials or steps of a claim, or to those that do not materially affect the basic characteristics of a claimed subject matter.

The terms "gastrointestinal tract," "GI tract," and "GI" may be used interchangeably herein and refer to an organ system in veterinary subjects which takes in food, digests the food to extract and absorb energy and nutrients, and expels the remaining waste. The GI tract is commonly considered to comprise two subparts: the upper GI tract (also "upper GI" herein) includes the buccal cavity, pharynx, esophagus, stomach, and duodenum, and the lower GI tract (also "lower GI" herein) includes the small and large intestines, the jejeunum, the ileum, the colon, the cecum, the rectum, the anal canal, and the anus.

The terms "MPA active agent" and "mycophenolic acid active agent" may be used interchangeably herein and refer to MPA or a MPA-based ingredient (e.g., of a veterinary composition of the present disclosure) that exerts a physiological or pharmacodynamic effect on a subject. MPA active agents comprise MPA and pharmaceutically acceptable salts, esters, prodrugs, homologs, hydrates or solvates thereof. In certain embodiments, a MPA active agent comprises sodium mycophenolate. In certain embodiments, a MPA active agent comprises MMF.

As used herein, the term "metabolite" refers to an intermediate or final product of full or partial metabolism of a drug by a subject. An "active metabolite" exerts a physiological effect (i.e., effecting a change on a physiological dynamic, process, or function that can be readily identified, determined, or discerned according to known methods such as by clinical assays or by clinical or non-clinical observations; non-limiting examples of physiological effects include a reduction in lymphocyte count, an increase or decrease in a serum or a urine concentration of an active agent or a metabolite, diarrhea, weight loss or gain, rash, ulcers, and the like) in the body following partial or full metabolism of the drug. An "inactive metabolite" produces little or no physiological effect. MPA is primarily metabolized by glucuronidation via the enzyme uridine diphosphate glucuronosyltransferase (UGT) in the gastrointestinal (GI) tract, liver and kidney. The major metabolite, MPA glucuronide (MPAG), has generally been thought to be inactive. Acyl MPAG (AcMPAG) is one of the at least 3 minor MPA metabolites which is pharmacologically active and has also been implicated in causing adverse side effects in the GI. Levels of MPA and its metabolites may be determined according to methods and procedures known to those of ordinary skill in the art, such as, for example, HPLC and EMIT (see, e.g., Shipkova et al., *Clin. Chem.* 46(3):365-372 (2000)).

As used herein, "bioavailability" refers to the fraction of a drug that is absorbed and therefore available to produce a physiological effect. Bioavailability may be measured by quantifying the AUC, by, for example, plotting serum concentration over time plots using labeled drugs and mass spectroscopy. Bioavailability can be measured in terms of "absolute bioavailablity" or "relative bioavailablity."

Absolute bioavailability ($F_{abs}$) relates to bioavailability when administered in a non-intravenous dosage form (e.g., oral tablet) compared with the same drug administered intravenously. Absolute bioavailability may be determined by comparing the AUC of the non-i.v. and i.v. forms, and correcting for the respective doses:

$$F_{abs} = (AUC_{non\text{-}intravenous}/AUC_{intravenous}) * (Dose_{intravenous}/Dose_{non\text{-}intravenous})$$

Relative bioavailability ($F_{rel}$) compares the bioavailability of two different dosage forms of a drug. The relative AUCs for each dosage form are compared and relative doses are used to normalize the calculation:

$$F_{rel} = (AUC_{dosageA}/AUC_{dosageB}) * (Dose_B/Dose_A)$$

Pharmacodynamics ("PD"), as used herein, refers to the biochemical or physiological effect or effects of a drug on a subject. PD may be described in the context of a dose-response relationship or a concentration-response relationship, and may encompass a range of desirable, undesirable, or neutral effects through mechanisms such as stimulating or depressing action through receptor agonism and downstream effects, blocking or antagonizing action, stabilizing action, exchanging, replacing, or accumulating substances (e.g., glycogen storage), conferring a direct beneficial chemical reaction, or conferring a direct harmful chemical reaction (e.g., cytotoxicity, mutagenesis, or irritation). PD values described herein with respect to MPA compositions and related methods include, for example, the level or activity of IMPDH (i.e., decreasing the level or activity of IMPDH, e.g., as the level of MPA increases), toxic effects on a veterinary subject administered an MPA active agent (e.g., diarrhea), autoantibody levels or activity, cytokine release rate or levels, inflammation, and B or T lymphocyte count(s) or functionality(ies).

"Autoimmune disease" and "autoimmune disorder" may be used interchangeably herein and refer to conditions in which the immune system of a subject aberrantly recognizes the subject's own cell(s) or tissue(s) as antigenic and produces an inflammatory response against the subject's cell(s) or tissue(s). In certain embodiments, compositions and methods according to the present disclosure are useful to treat an (i.e., one or more) autoimmune disease, such as, for example, celiac disease, diabetes mellitus type 1, Grave's disease, inflammatory bowel disease, multiple sclerosis, psoriasis, rheumatoid arthritis, systemic lupus erythematosus, Behçet's disease, pemphigus vulgaris, refractory incomplete systemic lupus erythematosus, lupus nephritis, immunoglobulin A nephropathy, small vessel vasculitides, scleroderma (systemic sclerosis or SSc), idiopathic thrombocytopenic purpura (ITP), myasthenia gravis, psoriasis, atopic dermatitis, pernicious anemia, vitiligo, autoimmune hemolytic disease, glomerulonephritis, immune cytopenias, meningoencephalomyelitis, subepidermal blistering autoimmune disease, immunobullous diseases, cutaneous vasculitis, recurrent erythema multiforme, erythema nodosum, lichen planus, cutaneous Crohn's disease, sarcoidosis, immune reactions associated with veterinary transplant or implant procedures (e.g., tissue transplants, grafts, and device implants), including host-versus-graft disease (HvGD) and other forms of implant rejection, hepatitis, and pyoderma gangrenosum. Blood disorders or diseases treatable according to the presently disclosed methods and compositions include, but are not limited to, aplastic anemia, immune mediated hemolytic anemia, and immune-mediated thrombocytopenia.

"Treat," "treatment," and "ameliorate," as used herein, refer to the prevention, lessening of the likelihood of, or medical management of a disease, disorder, or condition of a veterinary subject (i.e., a non-human mammal having a gastrointestinal tract and having one or more IMPDH or related enzyme that performs IMDPH activity. A veterinary subject according to the presently disclosed methods and compositions may but need not necessarily, be evaluated, diagnosed, or treated by a veterinarian or other veterinary care professional). In general, a dose or treatment regimen comprising a modified-release veterinary composition of the present disclosure is administered to the veterinary subject in an amount sufficient to elicit a therapeutic or prophylactic benefit. Therapeutic or prophylactic/preventive benefits include, but are not limited to: improved clinical outcome; lessening or alleviation of symptoms associated with a disease; reduced frequency of occurrence of symptoms; improved quality of life; longer disease-free status; diminishment of extent of disease, stabilization of disease state; delay of disease onset, progression; remission; survival; prolonged survival; or any combination thereof.

A "therapeutically effective amount" or "effective amount" of a MPA active agent or a modified-release veterinary composition of the present disclosure refers to an amount sufficient to result in a therapeutic effect, including: improved clinical outcome; lessening or alleviation of symptoms associated with a disease; decreased occurrence of symptoms; improved quality of life; longer disease-free status; diminishment of extent of disease; stabilization of disease state; delay of disease progression; remission; survival; or prolonged survival in a statistically significant manner. For example, a therapeutically effective amount of a MPA active agent according to the compositions and methods of the present disclosure may be an amount sufficient to reduce or delay (onset of) blood levels of the enzyme IMPDH or reduce or delay enzymatic activity of IMPDH, to reduce the number, proliferation, or activity of B or T lymphocytes, to prevent, reduce, or ameliorate an inflammatory response in a veterinary subject, to treat an autoimmune disease or disorder, or to prevent, reduce the severity of, or delay the onset of a rejection occurring in the course of a cell, organ, or tissue transplant or graft. When referring to an individual active ingredient, administered alone, a therapeutically effective amount refers to the effects of that ingredient alone. When referring to a combination, a therapeutically effective amount refers to the combined amounts of active ingredients that result in a therapeutic effect, whether administered sequentially, contemporaneously, or simultaneously.

As used herein, "modulating" means reducing, raising, hastening, delaying, or preventing an occurrence, or increasing or decreasing the intensity or efficiency of the occurrence being modulated, through either direct or indirect means. In the specific context of modulating IMPDH activity, modulating refers to reducing the level of functional IMPDH, delaying, or reducing the efficacy, efficiency, or intensity of IMPDH-mediated conversion of IMP to XMP, or any combination thereof.

The term "modified-release" is used to describe products that alter the timing and/or the rate of release of the drug substance in a way that deviates from immediate-release following administration. A modified-release dosage form is a formulation in which the drug-release characteristics of time course and/or location are chosen to accomplish therapeutic or convenience objectives not offered by immediate-release dosage forms such as immediate-release tablets or suspensions or other promptly dissolving or releasing dosage forms. Modified-release oral drug formulations include, for example, extended-release formulations (which allow a reduction in dosage frequency as compared to the same drug presented as an immediate-release (conventional) dosage form, e.g., controlled-release, sustained-release, and long-acting formulations); delayed-release formulations (which release an identifiable portion or portions of drug at a time other than promptly after administration, e.g., enteric-coated aspirin and other NSAID products); targeted-release formulations (which release the drug at or near the intended physiologic site of action, and may have either immediate- or extended-release characteristics); and orally disintegrating tablets (ODT), which disintegrate rapidly in the saliva after oral administration. The terms "modified-release," "controlled-release," "sustained-release," "extended-release," "long-acting," "targeted-release," and "delayed-release" may be used interchangeably herein to refer to the release of an administered MPA active agent in a way that deviates from immediate release following administration. As used herein, an "immediate release" dosage refers to any dosage form that is formulated to release or make available the active ingredient immediately upon administration. A modified-release composition according to the present disclosure may, in certain embodiments, be formulated or administered to achieve one or more of the following characteristics: release of a MPA active agent at or within a certain time following administration; release of a MPA active agent under specific physiological conditions (e.g., pH, temperature); release of a MPA active agent within a particular part of the body based on known, estimated, or predicted digestive, circulatory, or metabolic rates; release of a MPA active agent with, upon, or following administration with another reagent; in a predetermined amount; release of a MPA active agent for a predetermined amount of time; release of a MPA active agent according to particular release profile; or any combination thereof.

As used herein, a "modified-release layer" refers to a layer of material that provides release of a MPA active agent over a pre-determined time or period of time, or at a pre-determined rate, or otherwise along a release profile that does not include immediate release of a MPA active agent following administration. Examples of materials suitable for forming a modified-release layer include various polymers, such as cellulose polymers or acrylate polymers, cellulose acetates, cellulose acetate butyrates, ethyl cellulose, hydroxypropyl methyl cellulose, methyl cellulose polymers, EUDRAGIT® polymers for modified release, poly(vinyl acrylate) (PVA) polymers (e.g., KOLLIDON® series). A modified-release layer can be applied as a single layer. In specific embodiments, a modified-release layer includes multiple layers, optionally concentrically disposed on one another.

As used herein, "protective layer" refers to a layer of material that provides protection from degradation or dissolution to an ingested composition as it travels through the stomach.

The terms "pharmaceutically acceptable excipient or carrier" or "physiologically acceptable excipient or carrier," as used herein, refer to non-active biologically compatible vehicles, which are described in greater detail herein, that are suitable for administration to a human or other non-human mammalian subject and generally recognized as safe or not causing a serious adverse event. In certain embodiments, a pharmaceutically acceptable carrier includes food items or liquids to be administered to the subject. For example, a modified-release veterinary composition can be sprinkled on, sprayed on, or otherwise added to, or combined with, food, "treats," or water to be consumed by a veterinary subject. In certain other embodiments, a MPA composition of the present disclosure may be carried by (i.e., contained within, combined with, or coated on) a food item. Feeding regimes useful for practicing such embodiments are described herein.

As used herein, "statistically significant" refers to a p value of 0.050 or less when calculated using the Students t-test and indicates that it is statistically unlikely that a particular event or result being measured has arisen by chance.

MPA, MPA Active Agents, and Pharmacology Thereof

Mycophenolic acid ($C_{17}H_{20}O_6$; "MPA") is a nonnucleoside, noncompetitive, reversible inhibitor of the enzyme inosine 5′-monophosphate dehydrogenase (IMPDH), which catalyzes the synthesis of xanthine monophosphate (XMP) from inosine-5′-monophosphate (IMP). IMP→XMP is the rate-limiting step in the de novo synthesis of guanine nucleotides required for nucleic acid synthesis, proliferation, and differentiation cells, including B and T lymphocytes. By inhibiting IMPDH activity, MPA acts as an immunosuppressive agent. See, e.g., Arns, W., *Transplantation Proceedings* 39:88-93 (2007), the disclosure and methods of which are herein incorporated by reference in their entirety. MPA has the following basic structure shown in Formula I:

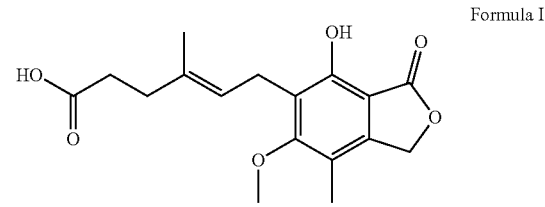 [SMILES: COc1c(C)c2c(c(O)c1C/C=C(\C)CCC(=O)O)C(=O)OC2]

Formula I

IMPDH has two isoenzymes, IMPDH1 and IMPDH2. The former is expressed in most cell types, while the latter predominates in activated lymphocytes (see, e.g., Winnicki et al., *Pharmacogenomics J.* 10(1):70-6 (2009)). MPA inhibits IMPDH2 up to 4- to 5-fold more than IMPDH1, and therefore has a more potent cytostatic effect on activated lymphocytes than on other cells.

MPA has been prepared for use in humans as an adjunctive immunosuppressant as a mycophenolate mofetil ester (MMF; approved for human use in the U.S. as Cellcept®) and as Na.MPA (Myfortic®).

Adverse drug reactions (≥1% of patients) associated with mycophenolate therapy (i.e., any single-dose or multi-dose therapeutic regimen involving use of MPA or an active agent thereof, as defined herein) include diarrhea, nausea, vomiting, joint pain, infections, leukopenia, and anemia. Sodium mycophenolate is also commonly associated with fatigue, headache, cough and/or breathing issues. Intravenous (IV) administration of MMF is also commonly associated with thrombophlebitis and thrombosis. Adverse effects associated with MMF use (0.1-1% of subjects) include esophagitis, gastritis, gastrointestinal tract hemorrhage, and/or invasive cytomegalovirus (CMV) infection. Less frequently, pulmonary fibrosis or various neoplasia occur, such as, for example, melanoma, lymphoma, and other malignancies, which MMF-related neoplasias can occur at frequencies of 1 in 20 to 1 in 200, depending on the type, with neoplasia in the skin being the most common site. Cases of pure red cell aplasia (PRCA) have also been reported.

Compositions and methods according to the present disclosure may be described in pharmacological terms, including pharmacokinetics ("PK") and pharmacodynamics ("PD"). As is understood in the art, pharmacokinetics relate to the fate—e.g., the concentration, metabolism, distribution, absorption, half-life, or excretion—of a drug administered to an organism. Non-limiting measures of PK include $C_{max}$ (the maximum serum concentration of a drug in a specified compartment or test area of the body), $T_{max}$ (the time at which the $C_{max}$ is observed), $C_{min}$ (minimum or trough concentration), $T_{min}$ (time at which $C_{min}$ is observed), $T_{1/2}$ (half-life of the drug or metabolite, i.e., the time taken for the drug concentration to fall to one half of its original value, which may be calculated using one or more points along the terminal phase of the elimination), elimination rate constant "k" (the slope calculated using one or more concentrations in the log domain the terminal phase), and AUC ("area under the curve"; the definite integral in a plot of concentration of a drug in blood plasma over time). AUC represents the total drug exposure over time in a given dose or dosing regimen, and may be computed starting at the time of administration and ending when the plasma concentration is minimal, or may be measured at chosen points in time and calculated therefrom.

PK values described herein with respect to WA compositions and related methods include, for example, [MPA] (concentration of mycophenolic acid drug), [MPAG], and [Acyl-MPAG]. Serum or plasma concentrations of a drug or metabolite may be reported in any appropriate unit, such as, for example, ng/mL, mg/kg, µg/mL, µg/L, and so on. Concentrations over time may be reported in any appropriate unit, such as, for example, µg*h/L or ng*h/mL. The AUC may be used to report the concentration over a given time interval ($AUC_t$) or unbound by a particular time interval ($AUC_{inf}$).

Other measures of MPA PK include, for example, drug: metabolite ratios, e.g., drug:metabolite ratios obtainable following administration of a MPA-containing agent (e.g., an immediate-release formulation or a modified-release formulation of the present disclosure). In certain embodiments, and as discussed further herein, compositions and methods of the present disclosure are useful to produce a higher (i.e., increased) MPA:metabolite ratio in a veterinary subject as compared to a reference MPA:metabolite ratio from a reference veterinary subject administered an immediate release reference dose of MMF, thereby decreasing the exposure of the (non-reference) veterinary subject to one or more MPA metabolites. Previous studies in humans and rats have shown MPA:metabolite ratios to be similar following IV or oral administration. With IV dosing, both intestinal and hepatic first-pass metabolism is bypassed. As a consequence, the MPA:metabolite ratio is expected to be higher based on IV administration. However, without wishing to be bound by theory, enterohepatic circulation may equalize the MPA: metabolite ratio between the oral and IV administration methods. Moreover, variable glucuronidation and efflux within the liver and gastrointestinal tract may result in differential formation of MPA metabolites over time.

Moreover, presently disclosed methods and compositions may, in some embodiments, possess desired MPA pharmacodynamics. For example, in some embodiments, presently disclosed methods and compositions of the present disclosure may be used for e.g., modulating IMPDH activity, reducing lymphocyte counts, immunosuppression, or modulating an inflammatory response in a veterinary subject.

Methods of Treatment and Administration

Compositions and methods disclosed herein may be useful in treating autoimmune disease, blood disorders including lymphocyte diseases, or transplant or graft rejection of (or by) native or transgenic organs, tissues, or cells, such as in tissue or cellular allograft or xenograft transplants. For example, in certain embodiments, presently disclosed methods and compositions are useful to treat celiac disease, diabetes mellitus type 1, Grave's disease, inflammatory bowel disease, multiple sclerosis, psoriasis, rheumatoid arthritis, systemic lupus erythematosus, Behçet's disease, pemphigus vulgaris, refractory incomplete systemic lupus erythematosus, lupus nephritis, immunoglobulin A nephropathy, small vessel vasculitides, scleroderma (systemic sclerosis or SSc), idiopathic thrombocytopenic purpura (ITP), myasthenia gravis, psoriasis, atopic dermatitis, pernicious anemia, vitiligo, autoimmune hemolytic disease, glomerulonephritis, immune cytopenias, meningoencephalomyelitis, subepidermal blistering autoimmune disease, immunobullous diseases, cutaneous vasculitis, recurrent erythema multiforme, erythema nodosum, lichen planus, cutaneous Crohn's disease, sarcoidosis, immune reactions associated with veterinary transplant or implant procedures (e.g., tissue transplants, grafts, and device implants), including host-versus-graft disease (HvGD) and other forms of implant rejection, hepatitis, and pyoderma gangrenosum. Blood disorders or diseases treatable according to the presently disclosed methods and compositions include, but are not limited to, aplastic anemia, immune mediated hemolytic anemia, and immune-mediated thrombocytopenia.

In any of the embodiments disclosed herein, a method may comprise administering a therapeutically effective amount of a modified-release veterinary composition of the present disclosure.

Modified Release of a MPA Active Agent

In embodiments, presently disclosed methods and compositions provide for modified release of a MPA active agent in a veterinary subject. In certain embodiments of the methods described herein, delivering, or biasing delivery of, MPA active agents to the lower GI tract of a veterinary subject increases the MPA:metabolite ratio as compared to a delivery that is not biased toward the lower GI tract. In examples of such embodiments, intracolonic administration of Na.MPA and oral administration of extended-release enteric-coated Na.MPA formulations were found to produce higher MPA:metabolite ratios than oral administration of MMF or enteric-coated Na.MPA. Such embodiments may provide advantages in dose efficiency (by increasing the amount of bioavailable MPA), sustained efficacy (slowed release of MPA active agent over time, targeted to areas of high WA absorption and lower MPA metabolism (i.e., the lower GI)), and decreased exposure to active metabolites associated with undesired side effects (e.g., AcMPAG). Furthermore, and without wishing to be bound by theory, a sudden "spike" in plasma [MPA] following administration of an immediate-release formulation is typically followed by a sharp decrease in [MPA]; that is, $C_{max}$ and $C_{min}$ occur close in time. Such release profiles may lead to toxicities, inefficient bioabsorption of the MPA, or failure to deliver the MPA to a site of interest (e.g., the lower GI).

Thus, achieving a more consistent WA release profile (e.g., $T_{max}$ and $T_{min}$ are further separated in time, [MPA] changes gradually, AUC is increased, or any combination thereof) may be advantageous. Accordingly, in some embodiments, a modified-release veterinary composition is administered in an amount effective to provide for an improved WA release profile in a veterinary subject relative to an immediate-release WA formulation (e.g., by providing sustained release of the MPA active over a longer time period as compared to a reference immediate-release formulation, or by providing improved bioavailability of MPA). In certain embodiments, compositions disclosed herein include delayed-release characteristics. For example, in some embodiments, a delayed-release type of modified-release formulation may be characterized by a $C_{max}$ occurring at a later time than a $C_{max}$ that occurs following administration of a reference immediate-release formulation. In further embodiments, the release of an administered MPA active agent may be at such a rate that total serum or blood levels the WA active agent are maintained or elevated above pre-dosing levels for an extended period of time, e.g., about 4 to about 24 hours or even longer. In certain embodiments, a composition according to the present disclosure has modified release of a WA active agent in the GI tract of a veterinary subject, such as, for example, preferential or primary release occurring in the lower GI tract.

In some embodiments, a method comprises delivering, via oral administration, a mycophenolic acid (MPA) active agent to a lower gastrointestinal tract of the veterinary subject in a modified release. Modified-release veterinary compositions according to the present disclosure are, in certain embodiments, formulated to preferentially release a MPA active agent in the gastrointestinal tract of veterinary subject following oral administration thereof. Preferably, at least a portion (e.g., a majority) of a MPA active agent comprised in a modified-release veterinary composition is delivered to and released within the lower GI tract (e.g., the large intestine). For example, in some embodiments, more (e.g., a greater proportion) of a MPA active agent comprised in a modified-release veterinary composition is released within the lower GI tract than in the upper GI tract. In certain embodiments concerning the treatment of canine veterinary subjects, for example, the majority of the MPA active agent (i.e., from at least about 50.1% to 100%) is released in the lower GI tract. In certain embodiments, a modified-release veterinary composition is formulated to provide release of at least some of the MPA active agent in the upper GI tract.

In some embodiments of the presently disclosed methods, a MPA active agent is released in a veterinary subject according to a schedule such as the following exemplary schedule:

| Hours Following Administration (Single Dose) | % MPA Active Agent Released |
| --- | --- |
| 0.5 | about 0.0 to about 1.0 |
| 2 | about 3.0 to about 10.0 |
| 2.5 | about 10.0 to about 30.0 |
| 3 | about 15.0 to about 40.0 |
| 4 | about 25.0 to about 55.0 |
| 6 | about 40.0 to about 75.0 |
| 7 | about 50.0 to about 80.0 |

-continued

| Hours Following Administration (Single Dose) | % MPA Active Agent Released |
| --- | --- |
| 10 | about 60.0 to about 90.0 |
| 14 | about 70.0 to about 100 |

In certain embodiments, a MPA active agent is released according to a schedule such as the following exemplary schedule:

| Hours Following Administration (Single Dose) | % NaMPA released |
| --- | --- |
| 0.5 | up to 0.9 |
| 1 | up to 3.2 |
| 2 | up to 7.9 |
| 2.5 | up to 25.1 |
| 3 | up to 35.8 |
| 4 | up to 51.3 |
| 5 | up to 61.4 |
| 6 | up to 67.9 |
| 7 | up to 72.8 |
| 8 | up to 76.2 |
| 10 | up to 81.5 |
| 14 | up to 86.9 |

In certain embodiments, a MPA active agent is released according to a schedule such as the following exemplary schedule:

| Hours Following Administration (Single Dose) | % NaMPA released |
| --- | --- |
| 0.5 | up to 0.0 |
| 1 | up to 1.5 |
| 2 | up to 4.9 |
| 2.5 | up to 13.2 |
| 3 | up to 21.4 |
| 4 | up to 31.7 |
| 5 | up to 40.7 |
| 6 | up to 48.0 |
| 7 | up to 54.0 |
| 8 | up to 59.1 |
| 10 | up to 66.1 |
| 14 | up to 76.1 |

A release rate or schedule may be determined according to standard techniques, such as, for example, a dissolution procedure comprising exposing a modified-release veterinary composition to pH 1.2 media for 2 hours, and thereafter moving the modified-release veterinary composition to pH 6.8 media, and analyzing media aliquots at periodic intervals (e.g., at 0.5, 1, 2, 2.5, 3, 4, 5, 6, 7, 8, 10, and 14 hours) for the presence of a MPA active agent, as performed in Example 1. In addition, known HPLC and RP-HPLC methods can be used to analyze the presence of a MPA active agent; see. e.g., RP-HPLC methods as described in Renner et al., *Analytical Chemistry* 73(1):41-6 (2001) or Reddy et al., *Asian Journal of Chemistry* 25(9):4788 (2013), which methods are herein incorporated by reference. Dissolution rates can also be determined according to the technique taught in Scheubel et al., *Dissolution Technologies*, February 2012, pp. 52-58 (available online at dissolutiontech.com/DTresour/201202Articles/DT201202_A06.pdf), which technique is also incorporated herein in its entirety.

In vitro and in vivo PK parameters can be correlated by establishing an in vitro-in vivo correlation (IVIVC). An IVIVC can be established using, for example, in vitro dissolution and in vivo absorption (measured by comparing the amount of drug administered versus the concentration of drug present in serum). IVIVC correlations (e.g., Level A, Level B, Level C) and related methodologies are known in the art and taught, for example, in Gonzalez et al., *Dissolution Technologies*, May 2015, pp. 35-41 (available online at dissolutiontech.com/DTresour/201505Articles/DT201505_A05.pdf and incorporated herein by reference).

PK parameters can be determined using commercially available software, e.g., WinNonlin v.6.4.

Methods for Achieving Certain MPA Pharmacokinetics

In some embodiments, a method comprises administering to a veterinary subject a modified-release composition, whereupon following the administration, the veterinary subject has a [MPA] AUC over a period of time that is increased by at least about 1.5×, at least about 2×, at least about 2.5×, at least about 3×, at least about 4×, at least about 5×, at least about 10×, or more, as compared to the [MPA] AUC of a reference veterinary subject administered an immediate-release formulation, over the same period of time.

In certain embodiments, a method comprises administering to a veterinary subject a modified-release veterinary formulation comprising a MPA active agent, whereupon following the administration, the veterinary subject has a plasma [MPA] $C_{max}$ that is lower than (e.g., is less than about 90%, less than about 80%, less than about 70%, less than about 60%, less than about 50%, less than about 40%, or less) a $C_{max}$ plasma [MPA] from a reference veterinary subject administered a reference immediate-release MPA formulation. In particular embodiments, a method comprises administering to a veterinary subject (e.g., a fed subject, as described herein) a modified-release composition of the present disclosure, whereupon following the administration, the veterinary subject has a $C_{max}$ plasma [MPA] of less than about 2500 ng/nL, less than about 2000 ng/mL, or less than about 1500 ng/mL. In certain such embodiments of the methods, a veterinary subject is administered a modified-release composition of the present disclosure and, following the administration, maintains a plasma [MPA] of more than about 500 ng/mL for at least about 3 hours, at least about 4 hours, or at least about 5 hours following $T_{max}$.

Additionally, the present disclosure provides methods for increasing the exposure of a veterinary subject to a MPA active agent, wherein the methods comprise orally administering to the subject a modified-release veterinary composition according to the present disclosure. By way of background, the in vivo efficacy of MPA is thought to be limited by glucuronidation of the phenolic oxygen in the liver. Without wishing to be bound by theory, it is believed that embodiments of the modified-release veterinary compositions of the present disclosure avoid at least some first-pass intestinal metabolism in a veterinary subject (e.g., a dog or a cat) administered a modified-release veterinary composition as described herein, thereby lowering the rate of glucuronidation of the MPA. In certain embodiments, the compositions thus improve the efficacy of the MPA active agent in vivo and, in particular embodiments, reduce the dose or dose frequency needed to achieve therapeutic benefits.

In certain embodiments of the methods, a veterinary subject has a MPA:metabolite ratio that is elevated as compared to a corresponding MPA:metabolite ratio obtained from a reference veterinary subject following administration of an immediate-release reference oral dosage of mycophenolate mofetil (MMF) thereto. In embodiments, a metabolite comprises MPAG, AcMPAG, or both. In certain embodiments, a MPA:metabolite ratio comprises MPA:MPAG, MPA:AcMPAG, or both. In come embodiments, a metabolite comprises MPAG, and the MPA:MPAG ratio (i.e., an absolute ratio within the subject) is from about 1:1 to about 10:1. In particular embodiments, a MPA:MPAG ratio is from about 1.5:1 to about 5:1, for example about 2:1. In other embodiments, a metabolite comprises AcMPAG, and a MPA:AcMPAG ratio is from about 50:1 to about 250:1. In particular embodiments, a MPA:AcMPAG ratio is about from 100:1 to about 200:1, for example about 150:1. In some embodiments, a MPA:MPAG ratio is from about 1:1 to about 10:1 and a MPA:AcMPAG ratio is from about 50:1 to about 200:2. In particular embodiments, a MPA:MPAG ratio is from about 1.5:1 to about 5:1, for example about 2:1, and a MPA:AcMPAG ratio is from about 100:1 to about 200:1, for example about 150:1.

In any of the disclosed embodiments, a method comprises administering a modified-release veterinary composition of the present disclosure.

Methods for Delivering MPA Active Agents

For disease management in veterinary subjects, various routes of drug administration are possible, including, for example, intravenous, oral, intracolonic, and subcutaneous delivery methods. However, injection and intracolonic methods may be time-consuming, require the direction or assistance of a veterinary care professional, and, importantly, may be highly uncomfortable and stressful for the veterinary subject. Thus, in certain embodiments, methods and modified-release veterinary compositions of the present disclosure concern oral administration of a MPA active agent. In certain embodiments, a modified-release veterinary composition may be administered by lavage, spray, or drinking water when the subject is in a fasted state or in a fed state, or with food that is provided to the subject. For example, in certain embodiments, a fasted state may comprise a state in which the veterinary subject was fed no later than about 1, 2, 3, 4, 5, 6, 7, 8, 9, 10, 11, 12, 14, 16, 18, 20, 24, or more hours prior to administration, and then optionally not fed again until about 1, 2, 3, 4, 5, 6, 7, 8, 9, 10, 11, 12, 14, 16, 18, or 24 hours following administration. A fed state may comprise a state in which the veterinary subject has been fed immediately prior to, or no more than 1 hour prior to, administration. In certain embodiments, modified-release veterinary compositions are mixed in, sprinkled on, or otherwise provided with the food so that is the compositions are ingested by the veterinary subject.

In some embodiments, a composition is administered to the subject under a multiple dose regime (e.g., under a NID, TID, QID, or PRN regime). It will be understood that the overall dosage administered, amount of MPA active agent released, and frequency of administration can be determined as desired in accordance with, for example, the state of health of the subject, the severity or development of the need for the MPA, the size, weight, age, metabolism, activity level, or other factors that may dictate the needs of the subject for the MPA active agent.

Modified-Release Veterinary Compositions

Figure 3:
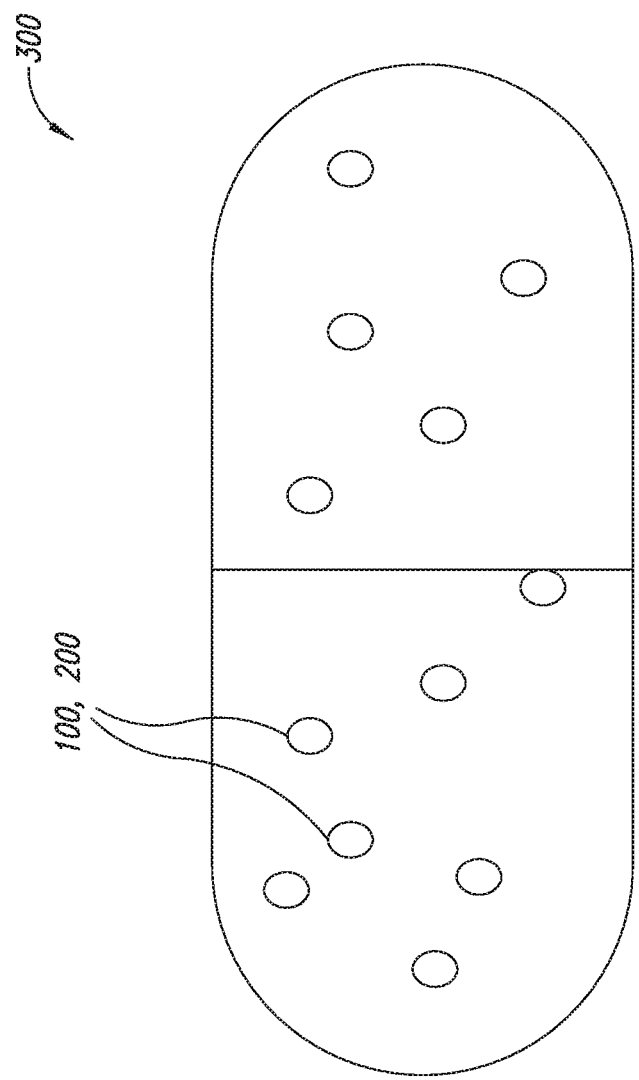
FIG. 3 shows a representation of an embodiment of capsule comprising a modified-release veterinary composition in accordance with the present disclosure.

Any of the embodiments of the methods according to the present disclosure may involve administering to the veterinary subject one or more of the compositions described herein. In certain embodiments, modified-release veterinary compositions of the disclosure, alone or in any combination, may be comprised in tablets, capsules, slurries, dragees, suspensions, chewables, or other forms suitable for oral administration. For example, as shown in FIG. 3, a capsule 300 includes a plurality of modified-release pharmaceutical compositions 100, 200, dispersed or mixed within the capsule 300.

Delivery of a MPA active agent to a veterinary subject may comprise administering a single type of a modified-release veterinary composition or may alternatively comprise administering multiple types of the modified-release veterinary compositions. For example, a mixture of modified-release veterinary compositions having different release characteristics may be administered so as to achieve a desired release profile. Thus, in certain embodiments, a plurality of modified-release veterinary compositions having cores of different sizes, or the presence or absence of a protective layer, or other characteristics may be administered to meet the needs of the veterinary subject. This flexibility advantageously permits selecting or calibrating a method for a specific veterinary subject (e.g., an individual animal) or for a sub-population of veterinary subjects (e.g., dog breeds) as may be warranted by characteristics such as the specific size, activity, level, responsiveness, general health, and other specific characteristics of the veterinary subject or subjects.

In certain embodiments, a modified-release pharmaceutical composition (FIG. 1, 100) includes a core and a MPA active agent. In certain such embodiments, a core 102 of a modified-release composition 100 comprises a solid support core, such as, for example, a sugar bead, a sugar sphere, a nonpareil bead, a microcrystalline cellulose bead, a silica bead, a calcium carbonate bead, a tartaric acid bead, a mannitol bead, a lactose bead, a starch bead, or another pharmaceutically acceptable core onto which an MPA active agent and other layers described herein can be disposed. In some embodiments, a core 102 comprises an active agent layer 104 disposed over at least a portion of the core 102 (e.g., disposed over a portion, or all, of the core 102). A MPA active agent may be disposed over core 102 using methods known in the art, such as, for example, spray coating, extrusion, suspension layering, dry powder layering, spray granulation, direct pelletizing, dip coating, layering, painting, deposition methods, and the like (see, e.g., methods outlined by Glatt GmbH, Binzen, Germany, www.glatt.com).

Figure 2:
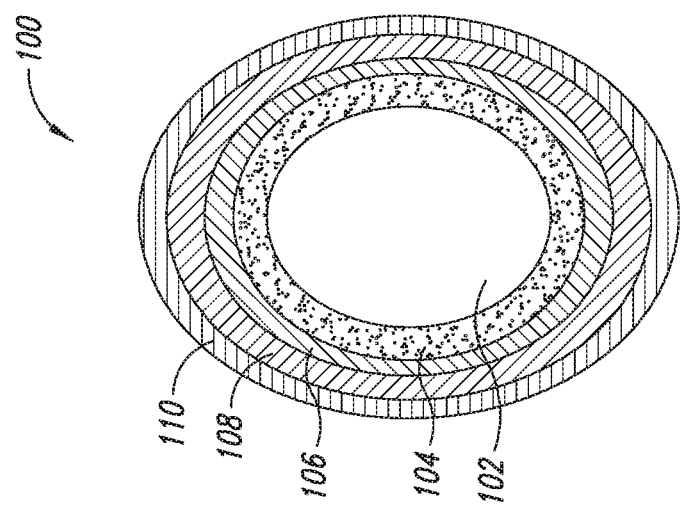
FIG. 2 shows a representation of an embodiment of a further modified-release veterinary composition in accordance with an embodiment hereof.

In alternative embodiments, as shown in FIG. 2, core 202 is an extruded core, in which a MPA active agent is dispersed or otherwise associated with core 202. Extruded cores can be prepared as described, for example, in U.S. Pat. Nos. 4,808,413 and 5,049,394 (the disclosures of each of which are incorporated by reference herein in their entireties), and may include a binder-plasticizer (e.g., a non-lipophilic binder-plasticizer (such as microcrystalline cellulose)), an excipient (e.g., a starch-based excipient) or a binder. Additional exemplary extruded cores can be prepared as described in Missaghi et al., "Investigation of Venlafaxine HCl Release from Extruded and Spheronized Beads Coated with Ethylcellulose Using Organic or Aqueous Coating Systems," Controlled-Release Society Annual Meeting July 2008, the disclosure of which is incorporated by reference herein in its entirety for all purposes.

For example, in certain embodiments, extruded core 202 includes a MPA active agent (e.g., sodium mycophenolate) from about 50 wt % to about 90 wt %, an extrusion/spheronization aid, such as microcrystalline cellulose, from about 10 wt % to about 30 wt %, or from about 15 wt % to 20 wt %. As used herein, the amount of a substance in a composition may be described "by weight," by "percent weight," or "wt %," meaning the weight of a substance relative to the weight of an individual composition (e.g., a single coated core) of the modified-release veterinary compositions, rather than relative to the total weight the modified-release veterinary compositions in a combination (e.g., of a capsule, tablet, slurry, or dragee containing a plurality of the coated cores). In certain embodiments, extruded core 202 further comprises one or more of: a binder (e.g., hydroxypropyl cellulose, hydroxyl propyl methyl cellulose, pregelatinized starch, ethyl cellulose or poly vinyl pyrrolidone) from about 1 wt % to about 10 wt %, preferably from about 2 wt % to about 5 wt %; a modified release excipient, such as, for example, hydroxpropyl methyl cellulose (HPMC), hydroxypropyl cellulose (HPC), acrylic polymers, hydroxyethyl cellulose (HEC), ethyl cellulose (EC), which can be incorporated into the beads or applied as coating; a filler, such as, for example, lactose, maltodextrin, mannitol, sorbitol, dicalcium phosphate, or the like; and a superdisintegrant, such as, for example, crosslinked poly(vinyl pyrrolidone) (PVP), sodium starch glycolate, or sodium croscarmellose, or the like.

In embodiments having extruded core 202, at least a portion of the MPA active agent can be dispersed, dissolved, mixed in, or otherwise distributed throughout core 202. For example, the MPA active agent may be co-dissolved with the various polymers and other excipients for producing the extruded cores, and then passed through an extruder to form the desired size beads, prior to drying. Methods suitable for making extruded cores according to the presently disclosed compositions are described in, for example, U.S. Pat. No. 5,049,394, which methods are incorporated herein by reference.

The size of core 102, 202 can be important to ensure sufficient delivery of a MPA active agent to a veterinary subject. For example, in certain instances it has been reported that canines do not readily pass objects above certain dimensions in the lower GI. Accordingly, in certain embodiments, a core 102, 202 has a diameter of about 0.5 mm to about 10 mm. For example, in some embodiments, a diameter of a core 102, 202 can be selected from about 0.5 mm to about 9 mm, about 1 mm to about 8 mm, about 1 mm to about 7 mm, about 1 mm to about 6 mm, about 1 mm to about 5 mm, about 2 mm to about 5 mm, about 2 mm to about 4 mm, or about 1 mm, about 2 mm, about 3 mm, about 4 mm, about 5 mm, about 6 mm, about 7 mm, about 8 mm, about 9 mm, or about 10 mm in diameter. In certain embodiments, the diameter of the core 102, 202 is less than about 5 mm, or is about 2 mm to about 4 mm. For example, in some veterinary subjects, a core diameter of less than about 5 mm allows the compositions to move readily through the stomach of a veterinary subject, in particular, through a canine stomach and into the upper and then lower gastrointestinal tract for delivery. For some veterinary subjects, compositions with cores having a diameter of greater than about 5 mm may remain in the stomach for an undesirably long period of time, thereby impacting the targeted delivery of the MPA active agent.

In addition, the crushing strength of the stomach of certain veterinary patients, such as canines, can be significantly higher than the crushing strength of a human stomach (about 1.5N (human) vs. about 3.2N (canine); (see, e.g., Kamba et al., Int. J. Pharmaceutics 228(1-2):209-217 (2001)). Thus, in particular embodiments, smaller-sized cores, such as cores having diameters of less than about 5 mm, may prevent a modified-release veterinary composition from being crushed in the stomach, which may cause premature (and therefore ineffective and possibly adverse) release of a MPA active agent in the stomach of the veterinary subject.

In certain embodiments, a MPA active agent is present in a modified-release veterinary composition at about 20 wt % to about 90 wt %. In certain embodiments, the amount of MPA active agent can be selected from about 20 wt % to about 80 wt %, about 30 wt % to about 80 wt %, about 30 wt % to about 70 wt %, about 30 wt % to about 60 wt %, about 30 wt % to about 50 wt %, or about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, or about 90 wt % of the composition.

In particular embodiments, modified-release veterinary compositions 100, 200 of the present disclosure further comprise a modified-release layer 108, 208 disposed over at least a portion of core 102 or 202. In embodiments where an active agent is disposed over at least a portion of core 102 as active agent layer 104, the modified-release layer 108 can be disposed over at least a portion of the active agent layer 104. In embodiments where core 202 is an extruded core comprising at least a portion of the active agent, a modified-release layer 208 is disposed over at least a portion of core 202.

Accordingly, in certain embodiments, a modified-release layer 108, 208 includes a polymer as described herein at about 5 wt % to about 50 wt %, or about 10 wt % to about 40 wt %, or about 20 wt % to about 30 wt %, or about 5 wt %, about 10 wt %, about 15 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, or about 40 wt %. In certain embodiments, the polymer may be an ethyl cellulose polymer. In still further embodiments, modified release layer 108, 208 may include a soluble component to modulate the permeability thereof. Release of a MPA active agent may be further adjusted by varying the thickness of one or more polymer layers utilized to form a modified-release layer (i.e., by varying the weight of the polymer layer) or by adding pore forming-agents to affect the permeability of the modified-release layer.

In any of the embodiments described herein, a modified-release veterinary composition 100, 200 may further include a protective layer 110, 210 disposed over at least a portion of modified-release layer 108, 208. In certain embodiments, a protective layer 110, 210 is selected or designed to delay release of at least a portion of the MPA active agent until the composition reaches the lower GI tract.

Where utilized, a protective layer 110, 210 may be a pH sensitive layer that can maintain integrity at the pH of stomach acid (e.g., roughly pH 1.2 to pH 4.5 in canines), but at least partially degrades once it reaches the small or large intestine (having a pH of about 4 to about 8 in canines). In certain embodiments, protective layer 110, 210 dissolves at a pH above about 6.0. It will be understood that the pH sensitivity of the protective layer, as well as the overall strength and release characteristics of the composition, may vary in accordance with the physiological characteristics of the veterinary subject to be treated (e.g., large canine versus small canine, canine versus feline, bovine, etc.). Examples of suitable materials for forming protective layer 110, 210 include enteric polymers, such as methacrylate-based polymers such as EUDRAGIT® L or EUDRAGIT® S polymers, cellulose acetate phthalate, cellulose acetate succinate, HPMC phthalate, HPMC acetate succinate, sodium alginate, zein, polyvinyl acetate phthalate (PVAP), shellac, methacrylic aid-ethyl acrylate copolymer (Kollicoat MAE), and mixtures thereof. In further embodiments, modified-release layer 108, 208 and protective layer 110, 210 can be designed so as to provide a timed release, rather than a pH-dependent release, of the MPA active agent, so that they enable the compositions to pass through the stomach intact and release (at least a portion of) MPA active agent in the small and/or large intestine, as desired.

In further embodiments, modified-release veterinary compositions of the present disclosure may include a seal coat 106, 206. As shown in the exemplary embodiment of FIG. 1, in a modified-release veterinary composition 100, seal coat 106 separates core 102 and active agent layer 104 from modified-release layer 108. In the exemplary embodiment represented in FIG. 2, a modified release veterinary composition 200 includes a seal coat 206 that separates modified-release layer 208 from core 202, which is an extruded core containing at least some (i.e., all or less than all) of the MPA active agent. In certain embodiments, a seal coat 106, 206 may be useful to separate, partially or fully, a MPA active agent from modified-release layer 108, 208 so as to reduce or eliminate interactions and degradation of the modified release layer or of the active agent. However, in embodiments where a non-aqueous coating method is used to apply the active agent layer 104 to core 102, degradation may be less of a concern and seal coat 106 may therefore be excluded or reduced in thickness. Exemplary compositions for use in seal coat 106, 206 include various cellulose polymers, including hydroxypropyl methylcellulose, poly (vinyl alcohol) (Opadry AMB, Kollicoat), hydroxypropyl methylcellulose, methyl cellulose, hydroxyethylcellulose, Opadry series, and the like.

In any of the embodiments described herein, a modified-release veterinary composition may further comprise a buffering agent or buffer to protect a MPA active agent from degradation by gastric acid. Accordingly, a buffer can be added to core 102, 202 or to active agent layer 104 surrounding core 102. In the case of extruded cores 202, the buffer may be added to core 202 or added to a layer 206, 208, 210 surrounding core 202 to provide buffering and to maintain the integrity and activity of the MPA active agent. Exemplary buffers for use in the compositions described herein include, but are not limited to, phosphate buffers, citrate buffers and acetate buffers.

Accordingly, in certain embodiments, a MPA active agent is administered to the veterinary subject in a modified-release composition comprising: (a) a core having a diameter of less than about 10 mm; (b) an active layer disposed over at least a portion of the core and comprising the MPA active agent; (c) a seal coat disposed over the active layer; and, (d) a modified-release layer disposed over the seal coat layer and comprising about 5 wt % to about 50 wt % of the modified release veterinary composition, wherein the MPA active agent is about 20 wt % to about 90 wt % of the modified release veterinary composition and the modified release layer is about 5 wt % to about 50 wt % of the modified release veterinary composition. In alternative embodiments, a MPA active agent is administered to a veterinary subject in a modified-release veterinary composition comprising: (a) an extruded core having a diameter of less than about 10 mm; (b) the MPA active agent disposed at least partially within the core; (c) a seal coat disposed over the MPA active agent and the core; and, (d) a modified-release layer disposed over the seal coat layer, wherein the MPA active agent is about 20 wt % to about 90 wt % of the modified release veterinary composition and the modified release layer is about 5 wt % to about 50 wt % of the modified release veterinary composition.

In any of the embodiments disclosed herein, a modified-release layer may comprise a cellulose polymer, an acrylate polymer, a cellulose acetate, a cellulose acetate butyrate, an ethyl cellulose, a hydroxypropyl methyl cellulose, a methyl cellulose polymer, a poly(vinyl acrylate) (PVA) polymer, or any combination thereof. In certain embodiments, a modified-release layer comprises from about 15 wt % to about 35 wt % of the composition. In certain embodiments, a modified-release layer may comprise ethyl cellulose, such as in the form of an aqueous ethyl cellulose rate-controlling polymer. A modified-release layer may be applied in any way that provides an appropriate rate controlling membrane. For example, a powder coating may be used as a deposition vehicle for the modified-release layer. Any suitable dispersion product may be used, such as, for example, Surelease (Colorcon, Harleysville, Pa., USA) or other products and materials known in the art.

In certain embodiments, a modified-release layer may comprise ethyl cellulose, which may comprise aqueous ethyl cellulose rate-controlling polymer. In certain embodiments, a modified-release layer comprises a methacrylate polymer from about 10 wt % to about 30 wt %, which may be a EUDRAGIT polymer. In certain embodiments, a methacrylate polymer comprises one or both of EUDRAGIT RS100 and RL100. Where both EUDRAGIT RS100 and RL100 are present, in particular embodiments, they may be combined in about a 90:10 ratio. Alternatively, any desired polymer ratio, using any polymer blend, may be employed using known techniques to produce a composition having a desired release profile.

In any of the embodiments disclosed herein, a modified-release veterinary composition may further comprise a protective layer disposed over the modified release layer. For example, one or more polymers of the Eudragit L series (Evonik, Essen, Del.), such as L100, may be used to form a protective layer. In certain embodiments, a protective layer comprises from about 8 wt % to about 15 wt % of the composition. In certain embodiments wherein a composition comprises an extruded core, the composition may include a MPA active agent from about 50 wt % to about 90 wt %, and may optionally further comprise one or more of the following: an extrusion aid from about 10 wt % to about 30 wt %; a binder from about 1 wt % to about 10 wt %; a release excipient; a filler; and a superdisintegrant.

In any of the embodiments described herein, a modified-release veterinary composition may further comprise a buffer to affect stability or release of the MPA active agent under certain pH conditions.

In any of the embodiments disclosed herein, a MPA active agent may comprise sodium mycophenolate.

In certain embodiments, a modified-release veterinary composition is comprised in a dissolvable tablet, minitablet, a dissolvable minitablet, a capsule, a dragee, a slurry, a sachet, a chewable tablet, a buccal or sublingual dissolvable film or strip, a suspension, or any combination thereof.

It will be understood that a variety of dosages may be administered to a veterinary subject in accordance with, e.g., the physiological characteristics of the veterinary subject (e.g., size, GI length, digestive rate, digestive pH, stomach crushing strength), the state of health of the veterinary subject (e.g., the urgency of the need for treatment and of what strength) and other factors. For example, in certain embodiments, a dosage regime comprises a single administration of a single dose of a MPA composition (e.g., a modified-release veterinary composition as described herein). In certain embodiments, a dosage regime comprises multiple administrations of a single dose over the course of, e.g., a day. Alternatively, a dosage regime may comprise single or multiple administrations of multiple doses of a MPA composition. In embodiments comprising multiple doses, the doses may be administered simultaneously, contemporaneously, or sequentially.

In certain embodiments, methods, following administration according to the presently disclosed methods, a Cmax plasma [MPA] t of about 1 μg/mL to about 10 μg/mL is achieved in a veterinary subject. In certain embodiments, following administration, a Cmax plasma [MPA] of about 1 μg/mL to about 10 μg/mL for about 4 to about 24 hours is achieved in a veterinary subject. In certain embodiments, following administration, a Cmax plasma [MPA] of about 3 μg/mL to about 5 μg/mL for about 8 to about 24 hours is achieved in a veterinary subject.

In certain embodiments, following administration, a Cmax plasma [MPA] of about 5 to about 6 μg/mL is achieved in a veterinary subject and about 2.5 μg/mL/h to about 5 μg/mL of a MPA active agent is released in a veterinary subject for about 4 to about 10 hours. In certain embodiments, following administration, a Cmax plasma [MPA] in a veterinary subject of about 6 μg/mL is achieved.

In any of the embodiments disclosed herein, a veterinary subject has or is suspected of having an autoimmune disease or disorder, a blood disorder associated with IMPDH activity, or is having, is about to undergo, or has recently had a transplant or graft procedure. In certain embodiments, a subject has or is suspected of having an autoimmune disease or disorder selected from hepatitis, systemic lupus erythematosus, lupus nephritis, psoriasis, myasthenia gravis, IMHA, and atopic dermatitis.

In any of the embodiments disclosed herein, a MPA active agent may be administered when a veterinary subject is in a fed state, in a fasted state, or during a feeding (in which case, a MPA active agent or modified-release veterinary composition may be sprinkled on or mixed with food). In any of the embodiments disclosed herein, a veterinary subject may be a dog, a cat, or a primate. In certain embodiments, the veterinary subject is a dog or a cat.

In certain embodiments, the administration of a MPA active agent (e.g., via a modified-release veterinary composition described herein) occurs once per day, twice per day, or more frequently (e.g., 3-4 times per day) or less frequently (e.g., once every 26, 28, 30, 32, 34, 36, 38, 40, 42, 44, 46, or 48 hours or more), and can be adjusted in accordance with, for example, the responsiveness, activity level, general health, and needs of the veterinary subject.

EXAMPLES

Example 1

Preparation and Testing of Certain Mycophenolate Modified-Release Veterinary Compositions According to the Present Disclosure Preparation of Active Agent Coated Beads:
  Materials
  Sugar spheres (#25/30; COLORCON®, Harleysville, Pa.)
  OPADRY® Clear, hydroxypropyl methylcellulose-based coating (COLORCON®, Harleysville, Pa.)
  Purified Water
  Sodium Mycophenolate
  Equipment
  Mechanical stirrer
  Fluid bed coater
  Hot air oven

TABLE 1

| Composition of drug coating solution | |
|---|---|
| Component | Batch formula (g) |
| OPADRY ® Clear | 25 |
| Purified Water | 475 |
| Sodium Mycophenolate | 240 |

1. OPADRY® Clear was dispersed in purified water and stirred until a clear solution was obtained.
2. Mycophenolate sodium was added to the solution and stirred for 1 hour.
3. 500 g of sugar beads as loaded into the fluid bed chamber.
4. The bed was fluidized, sugar beads were warmed and the coating solution prepared as described in Table 1 was sprayed onto the fluidized beads.
5. Coating was continued with periodic drying and weighing of the coated beads.
6. Coating was continued until the beads had gained approximately 40% in weight.
7. Beads were dried overnight (15 hours) at 40° C. in a hot air oven Exemplary Preparation of Extruded Beads with Active Agent:
  Materials
  Drug Substance: Sodium mycophenolate: 50 to 90%
  Extrusion/Spheronization Aid: Microcrystalline Cellulose: 15 to 20%
  Binders: Hydroxypropyl cellulose or hydroxyl propyl methyl cellulose or Pregelatinized Starch or Ethyl Cellulose or poly(vinyl pyrrolidone) (2 to 5%)
  Modified release excipients: HPMC, HPC, acrylic polymers, HEC, EC—these can be incorporated into the beads or applied as coating
  Other fillers: lactose, maltodextrin, mannitol, sorbitol, dicalcium phosphate/(as needed)
  Superdisintegrants: crosslinked PVP, sodium starch glycolate, sodium croscarmellose (% as needed)
  Manufacturing
  The drug substance was mixed with microcrystalline cellulose, binder, and disintegrant in a planetary mixer or a high shear mixer for 10 minutes;
  The required amount of water was added to the mixer and mixing continued for another 5 to 10 minutes;
  The resulting wet mass was passed through an extruder to obtain an extrudate (example equipment: Caleva, LCI, Glatt etc.);
  The extrudate was then spheronized on a spheronizer fitted with a crosshatch plate to form spheronized beads (example equipment: Caleva, LCI, Glatt)
  The spheronized beads were then dried in a fluid bed dryer till the desired moisture content (<1%) was reached;
  The dried beads were then passed through screens to remove fine beads (<500 μm) and coarse beads (≥2500 μm);
  The dried beads were then loaded into a fluid bed coater and coated with an appropriate amount of a rate-controlling polymer (15 to 30% range);
  Additional enteric coating (optional) was then applied to the coated beads;
  The beads were then dried after all coating steps were completed.

Preparation of Seal Coated Beads:
  Materials
  Drug coated or extruded beads (from above sections)
  OPADRY® Clear
  Talc Purified Water
  Equipment
  Mechanical stirrer
  Fluid bed coater
  Hot air oven 1. OPADRY Clear was dispersed in purified water and stirred to obtain a clear solution.
2. Talc was dispersed into the OPADRY® solution and stirred to obtain a smooth dispersion.
3. About 300 g of the drug coated beads (from above) was loaded into the fluid bed coater.
4. The bed was fluidized, drug coated beads were warmed, and the coating solution prepared as described in Table 2 was sprayed onto the fluidized beads.
5. Coating was continued with periodic drying and weighing of the coated beads.
6. Coating was continued until the beads had gained approximately 8 to 10% in weight.
7. Beads were dried overnight (15 hours) at 40° C. in a hot air oven.

TABLE 2

| Composition of seal coat solution | |
|---|---|
| Component | Batch formula (g) |
| OPADRY ® Clear | 10 |
| Talc | 20 |
| Purified water | 170 |

Preparation of Modified-Release Layers:
  SURELEASE® Coating—Option 1
  Materials
  Seal Coated beads (from above)
  SURELEASE® E-7 19040, aqueous ethylcellulose rate controlling polymer (COLORCON®, Harleysville, Pa.) (Other grades of SURELEASE® can be used if desired)
  Equipment
  Mechanical stirrer
  Fluid bed coater
  Hot air oven

TABLE 3

| Composition of SURELEASE ® Coating solution | |
|---|---|
| Component | Batch formula (g) |
| SURELEASE ® E7 19040 | 240 |
| Purified water | 170 |

1. SURELEASE® was dispersed in purified water and stirred to obtain a smooth dispersion.
2. About 300 g of the seal coated beads was loaded into the fluid bed coater.
3. The bed was fluidized, the seal coated beads were warmed, and the coating solution prepared as described in Table 3 was sprayed onto the fluidized beads.
4. Coating was continued with periodic drying and weighing of the coated beads.
5. Coating was continued until the beads had gained desired coating weight.
6. Coated bead samples were withdrawn at desired weight gain (e.g.: 15%, 22%, 30%).
7. At the end of the coating, beads were dried overnight in the oven at 60° C./75% relative humidity conditions.

EUDRAGIT® Coating—Option 2
Materials
Seal Coated beads (from above)
EUDRAGIT® RS (acrylic modified-release polymer either as powder or premade dispersion—RS 30D)
EUDRAGIT® RL (acrylic modified-release polymer either as powder or premade dispersion—RL 30D)
Talc
Triethyl citrate (TEC)
Equipment
Mechanical stirrer
Fluid bed coater
Hot air oven

TABLE 4

Sample composition for EUDRAGIT® coating

| Component | Batch formula (g) |
|---|---|
| EUDRAGIT® RL 30D (1 part)* | 39.3 |
| EUDRAGIT® RS 30D (9 parts)* | 352.9 |
| TEC | 23.5 |
| Talc | 58.8 |
| Purified Water | 525.5 |

*This composition will be referred as EUDRAGIT® RS (90): RL (10) or EUDRAGIT® RS/RL: 90/10. This ratio can be altered in any composition, increasing amount of RS 100 will reduce membrane permeability with decrease in release rate from bead.

1. Talc and TEC were dispersed in purified water and homogenized until a smooth dispersion is obtained.
2. The dispersion from Step (1) was mixed until a uniform dispersion was obtained.
3. The dispersion was filtered through 80 mesh sieve to remove any coarse particles.
4. About 300 g of seal coated beads was loaded into the fluid bed coater.
5. The bed was fluidized, seal coated beads were warmed and the coating solution prepared as described in Table 4 was sprayed onto the fluidized beads.
6. Coating was continued with periodic drying and weighing of the coated beads until the desired weight gain was obtained (typically 15% to 30%).
7. Coated beads were dried overnight (15 hours) at 40° C. in a hot air oven.

E.R. Coating—Option 3
Materials
Ethylcellulose 10
Klucel EF (HPC)
Talc
Dibutyl sebacate
DI water
Ethanol
Equipment
Mechanical stirrer
Fluid bed coater
Hot air oven
Sprayer

TABLE 5

Sample composition for 30 wt % gain

| Component | Wt % |
|---|---|
| Ethylcellulose 10 | 4.15 |
| Klucel EF (HPC) | 0.46 |
| Talc | 0.92 |

TABLE 5-continued

Sample composition for 30 wt % gain

| Component | Wt % |
|---|---|
| Dibutyl Sebacate | 0.46 |
| DI water | 9.40 |
| Ethanol 190 pf | 84.61 |

1. Dibutyl sebacate was dissolved in a mixture of ethanol and deionized water.
2. The required quantity of HPC was dispersed in the hydroalcoholic mixture and stirred to obtain a solution.
3. The required quantity of ethylcellulose was dispersed in the above mixture and stirred until a solution was obtained
4. Talc was dispersed in the above solution and stirred to obtain a smooth dispersion.
5. The drug coated beads were loaded into the fluid bed coater
6. The bed was fluidized, beads were warmed, and the coating solution prepared as described in step 4 was sprayed onto the fluidized beads.
7. Coating was continued with periodic drying and weighing of the coated beads
8. Coating was continued until the beads had gained desired coating weight.
9. Coated bead samples were withdrawn at desired weight gain (e.g., 15%, 22%, or 30%)
Preparation of Protective Layer:
Materials
Control release layer coated beads (from above)
EUDRAGIT® L30 D 55 (other grades of EUDRAGIT® polymers, or OPADRY® polymers that confer enteric protection can also be used)
Triethyl citrate (TEC)
Talc
Equipment
Mechanical stirrer
Fluid bed coater
Hot air oven

TABLE 6

Composition of Enteric Coating solution

| Component | Batch formula (g) |
|---|---|
| EUDRAGIT® L30D 55 | 83.3 |
| TEC | 2.5 |
| Talc | 12.5 |
| Purified Water | 101.6 |

1. Talc and TEC were dispersed in purified water and homogenized until a smooth dispersion was obtained.
2. The dispersion from Step (1) was dispersed into EUDRAGIT® L30D 55 suspension and mix until a uniform dispersion was obtained.
3. The dispersion was filtered through 80 mesh sieve to remove any coarse particles.
4. About 300 g SURELEASE® coated beads was loaded into the fluid bed coater; alternatively, about 300 g of EUDRAGIT® coated beads from above may be used.
5. The bed was fluidized, modified-release coated beads were warmed and the coating solution prepared as described in Table 6 is sprayed onto the fluidized beads.
6. Coating was continued with periodic drying and weighing of the coated beads until the desired weight gain of EUDRAGIT® L 30 D55 was obtained (typically 8 to 15%).

7. Coated beads were dried overnight (15 hours) at 40° C. in a hot air oven.

Determination of Release Rate

Release rate determinations were performed on beads obtained after coating with modified-release layer(s) and optionally a protective layer. Release rate determinations were conducted as follows:

Dissolution Apparatus: USP Type 1

Dissolution Media Volume and Speed: 900 mL at 100 rpm

A known quantity of beads were weighed (based on assay of coated beads) and placed in the USP Type 1 basket apparatus. For a biphasic dissolution profile (biphasic media), beads were exposed to pH 1.2 media for 2 hours. After 2 hours, the basket was moved to buffer media at pH 6.8 and dissolution was continued for an additional 10 hours, 12 hours, 14 hours or 24 hours, as desired. Aliquots were withdrawn at periodic intervals and analyzed for mycophenolate sodium using a UV detection method. Data from representative experiments are shown in FIGS. 6-9 and Table 7, below.

Figure 4:
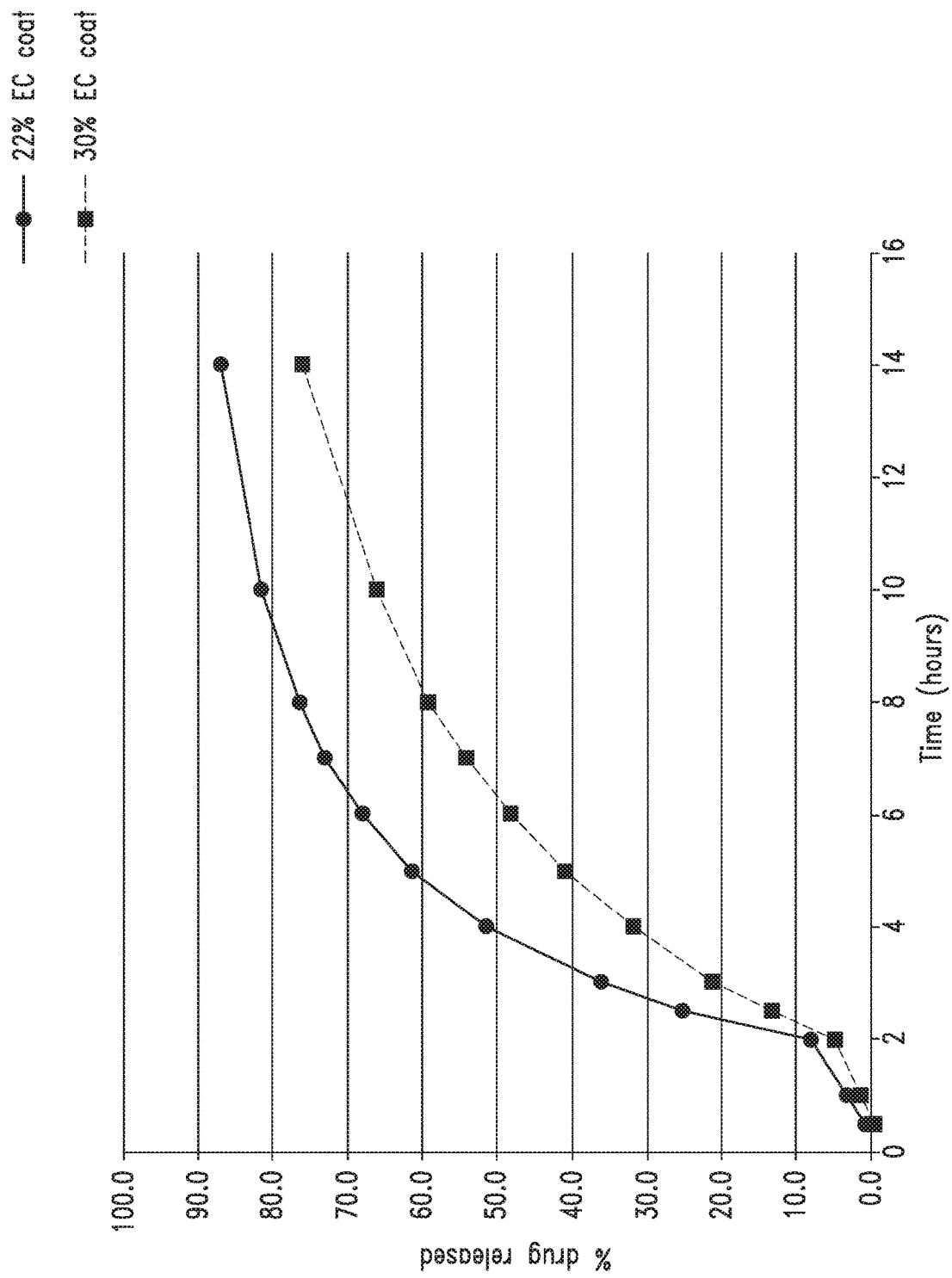
FIG. 4 shows the release of sodium mycophenolate from two embodiments of a modified-release veterinary composition in accordance with the present disclosure.

FIG. 4 shows the release of sodium mycophenolate from modified-release beads in biphasic media as noted above. The bead construct is sugar sphere/drug layer/HPMC seal coat/ethyl cellulose (SURELEASE®). The data was generated for beads with only a modified-release layer. A protective layer was not included. As shown, release from beads coated with a 22% by weight ethyl cellulose modified-release layer was higher than that for beads coated with a 30% by weight ethyl cellulose layer. Both compositions maintained their integrity at pH 1.2 (0-2 hours), with rapid release upon transitioning to pH 6.8 (>2 hours).

Figure 5:
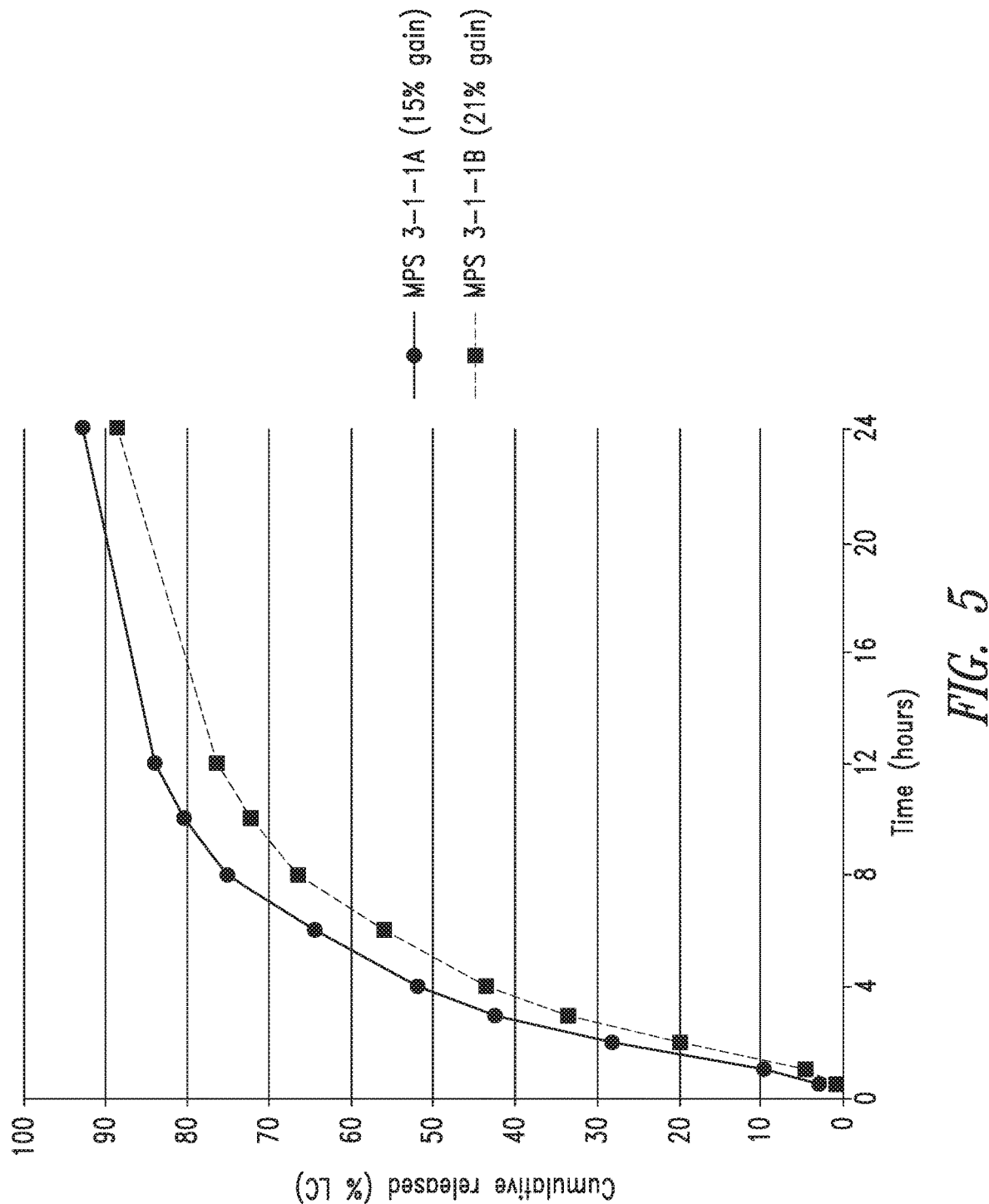
FIG. 5 shows the release of sodium mycophenolate from additional embodiments of a modified-release veterinary composition accordance with the present description.

FIG. 5 shows the release of sodium mycophenolate from modified-release beads in pH 6.8 media. The bead construct is sugar sphere/drug layer/HPMC seal coat/acrylic polymer (EUDRAGIT® RS 100). A protective layer was not included.

Figure 6:
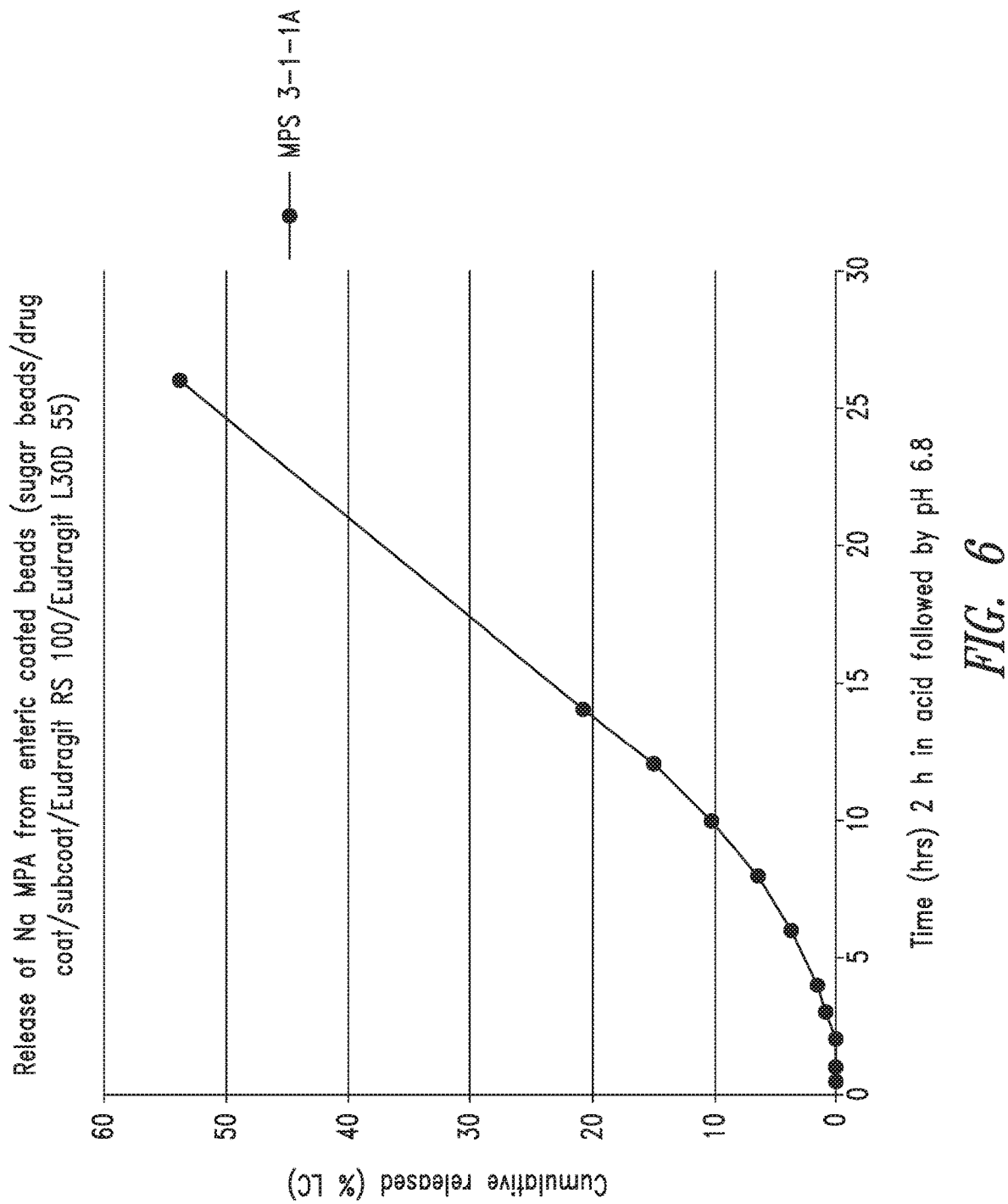
FIG. 6 shows the release of sodium mycophenolate from yet another embodiment of a modified-release composition in accordance with the present disclosure, where the composition is exposed to a 2-hour incubation in acidic media (pH 1.2), followed by 12 hours in pH 6.8 media.

FIG. 6 shows the release of sodium mycophenolate from modified-release beads in biphasic media, as described above. The bead construct is sugar sphere/drug layer/HMPC seal coat/EUDRAGIT® RS 100/EUDRAGIT® L30D 55. The EUDRAGIT® RS 100 layer provides the modified-release characteristics, while the EUDRAGIT® L30D 55 provides the protective, enteric coating. As noted, little to no release occurred at pH 1.2 (0-2 hours), with release occurring once the pH was raised to 6.8 (>2 hours).

Figure 7:
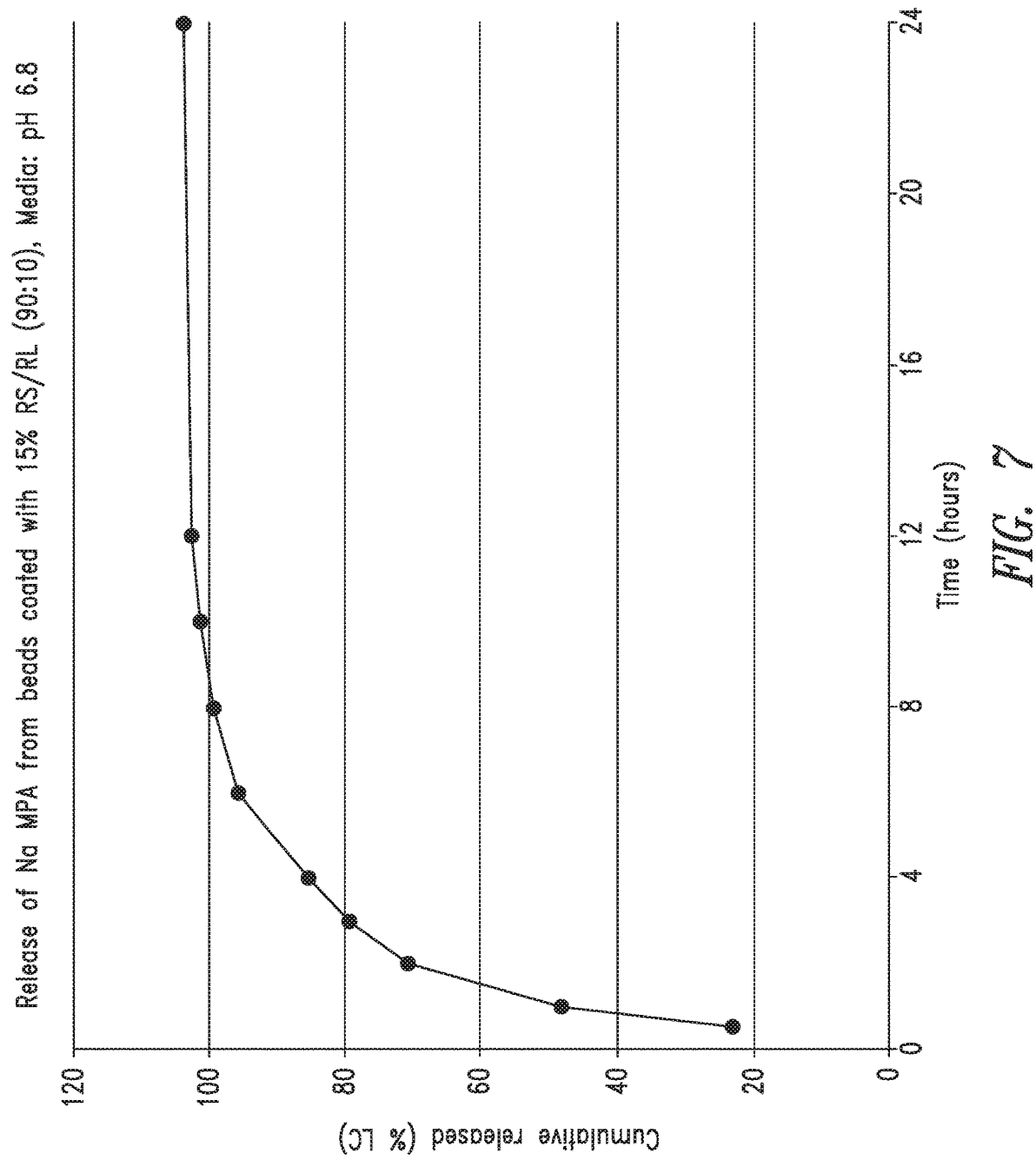
FIG. 7 shows release of sodium mycophenolate from another embodiment of a modified-release veterinary composition in accordance with the present disclosure.

FIG. 7 shows the release of sodium mycophenolate from modified-release beads in pH 6.8 media. The bead construct is sugar sphere/drug layer/EUIDRAGIT® RS 100:EUDRAGIT® RL 100 (90:10). A seal coat and a protective layer were not included. Rapid release is noted occurring around hours 2-6.

Figure 8:
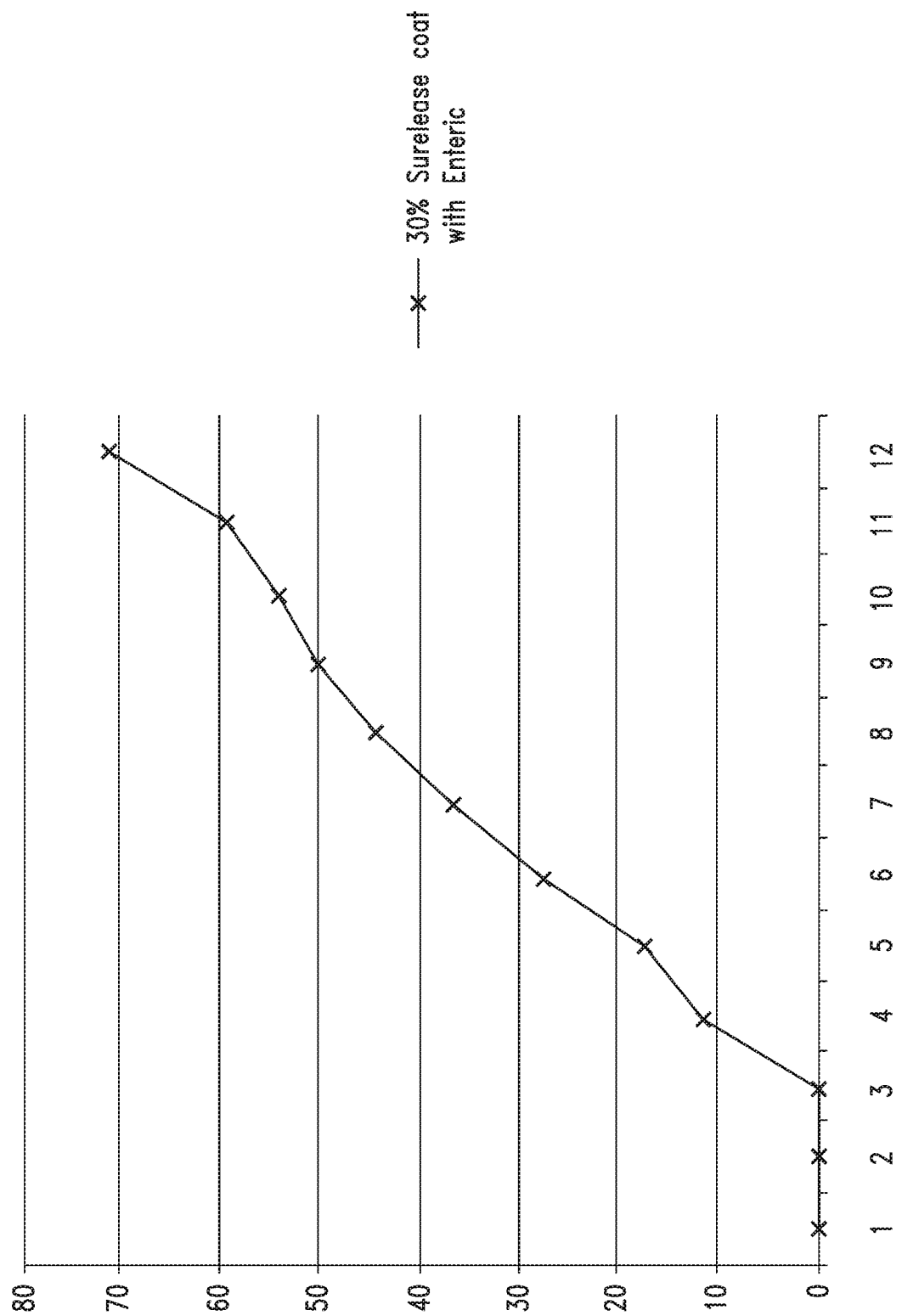
FIG. 8 shows release of sodium mycophenolate from yet another embodiment of a modified-release veterinary composition in accordance with the present disclosure where the composition is exposed to a 2-hour incubation in acidic media (pH 1.2), followed by 12 hours in pH 6.8 media.

FIG. 8 shows release of sodium mycophenolate from a modified release composition comprising 30 wt % Surelease polymer coat and a protective enteric coating. pH was switched from 1.2 to 6.8 following 2 h incubation.

Figure 9:
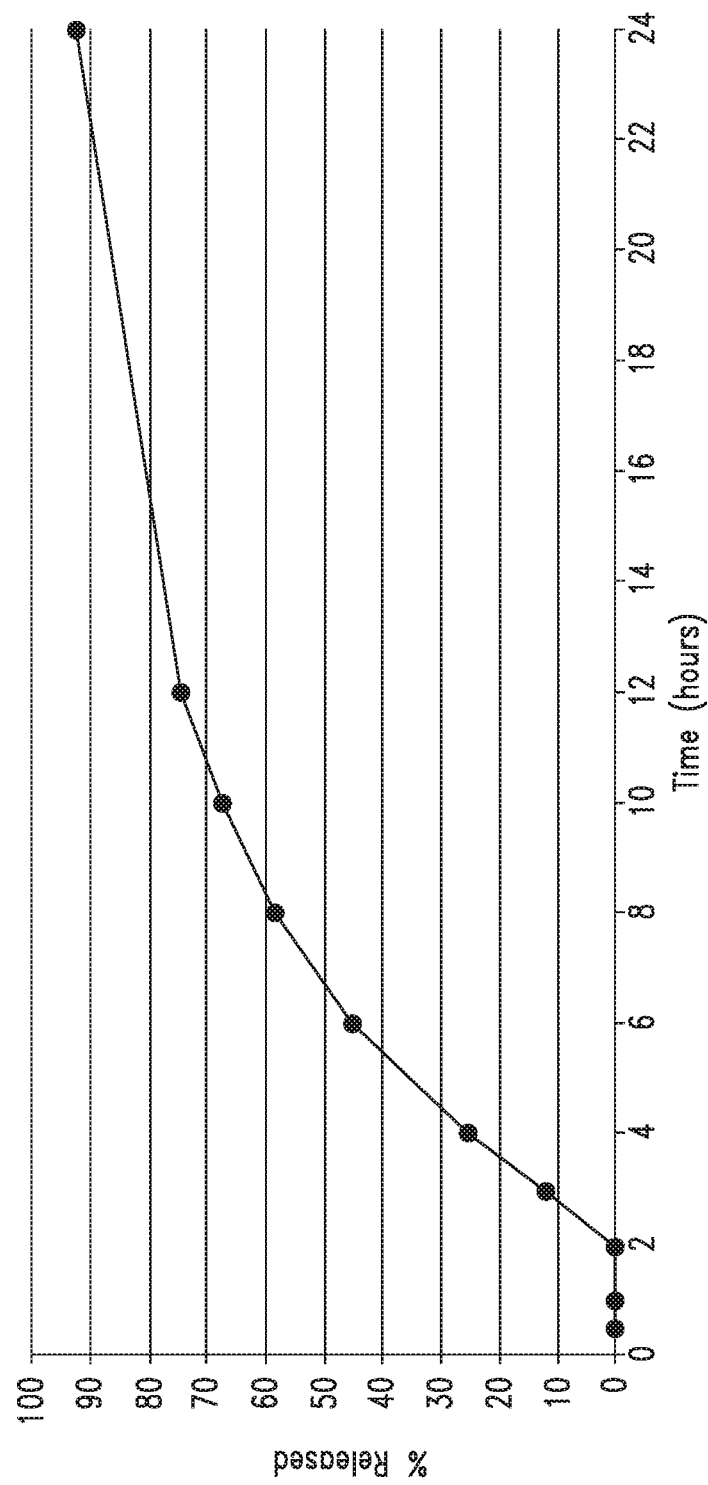
FIG. 9 shows release of sodium mycophenolate from an embodiment of a modified release veterinary composition according to the present disclosure, where the composition includes a solvent-based coating and where the composition is exposed to a 2-hour incubation in acidic media (pH 1.2), followed by 12 hours in pH 6.8 media.
Figure 10:
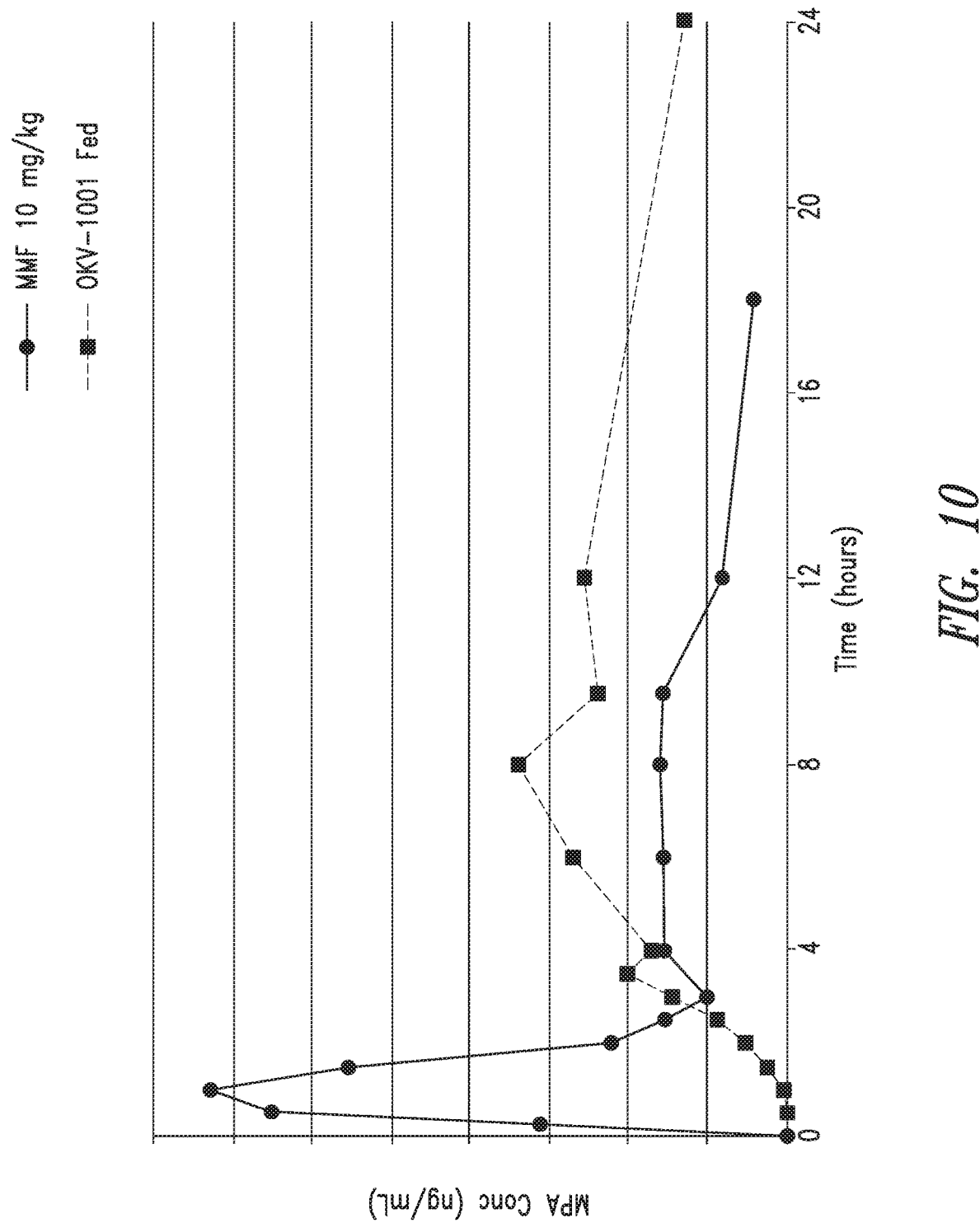
FIG. 10 shows relative levels of serum mycopenolic acid ([MPA]=ng/mL MPA) measured at the indicated timepoints following administration of either an immediate release mycophenolate mofetil solution (10 mg/kg MMF; circles) to fasted canines or a modified-release veterinary composition of the present disclosure to fed canines (270 mg MPA; squares).
Figure 11:
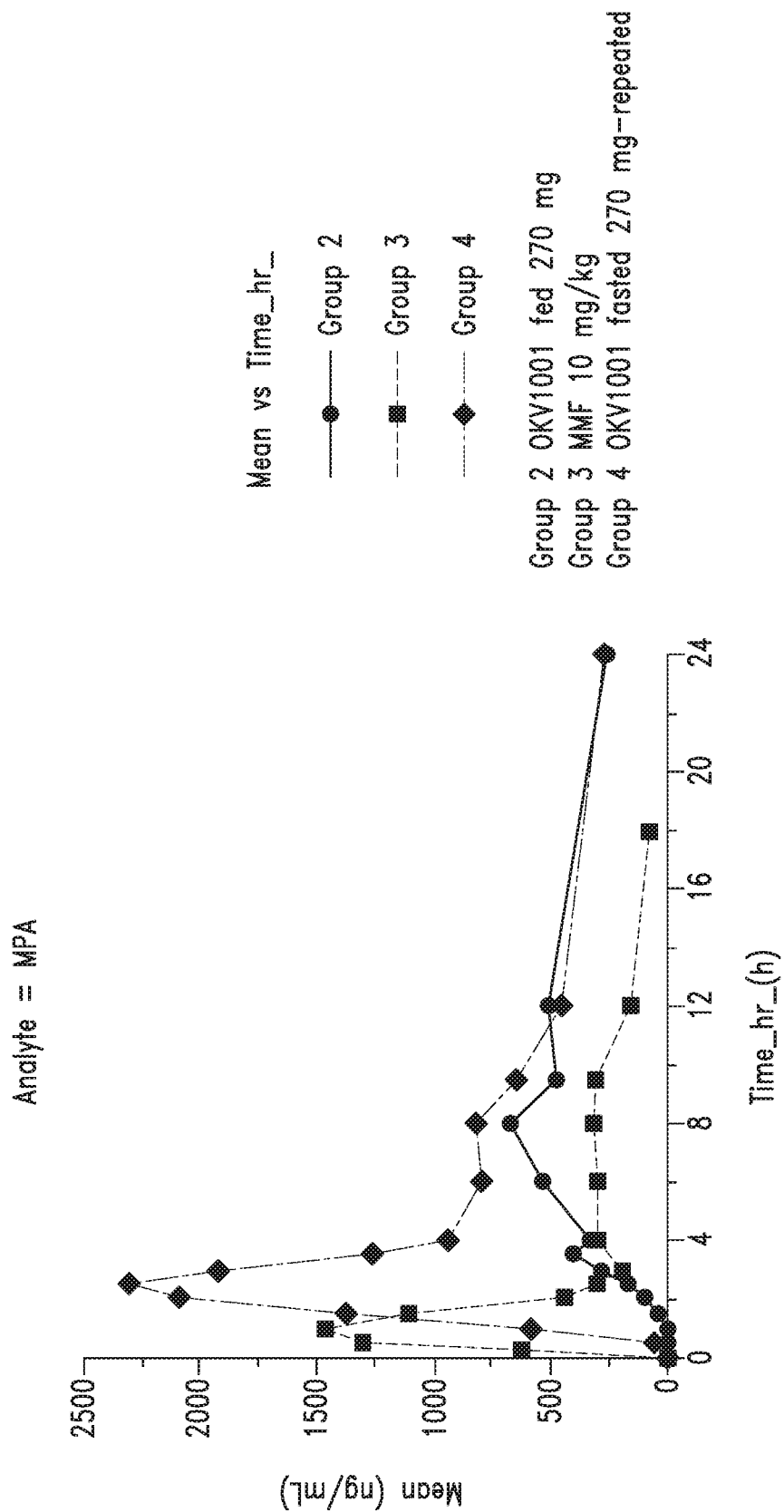
FIG. 11 shows another view of the data shown in FIG. 10 and further provides mean serum levels (ng/mL) of MPA in fasted canines following administration of the modified-release veterinary composition ("Group 4").
Figure 12:
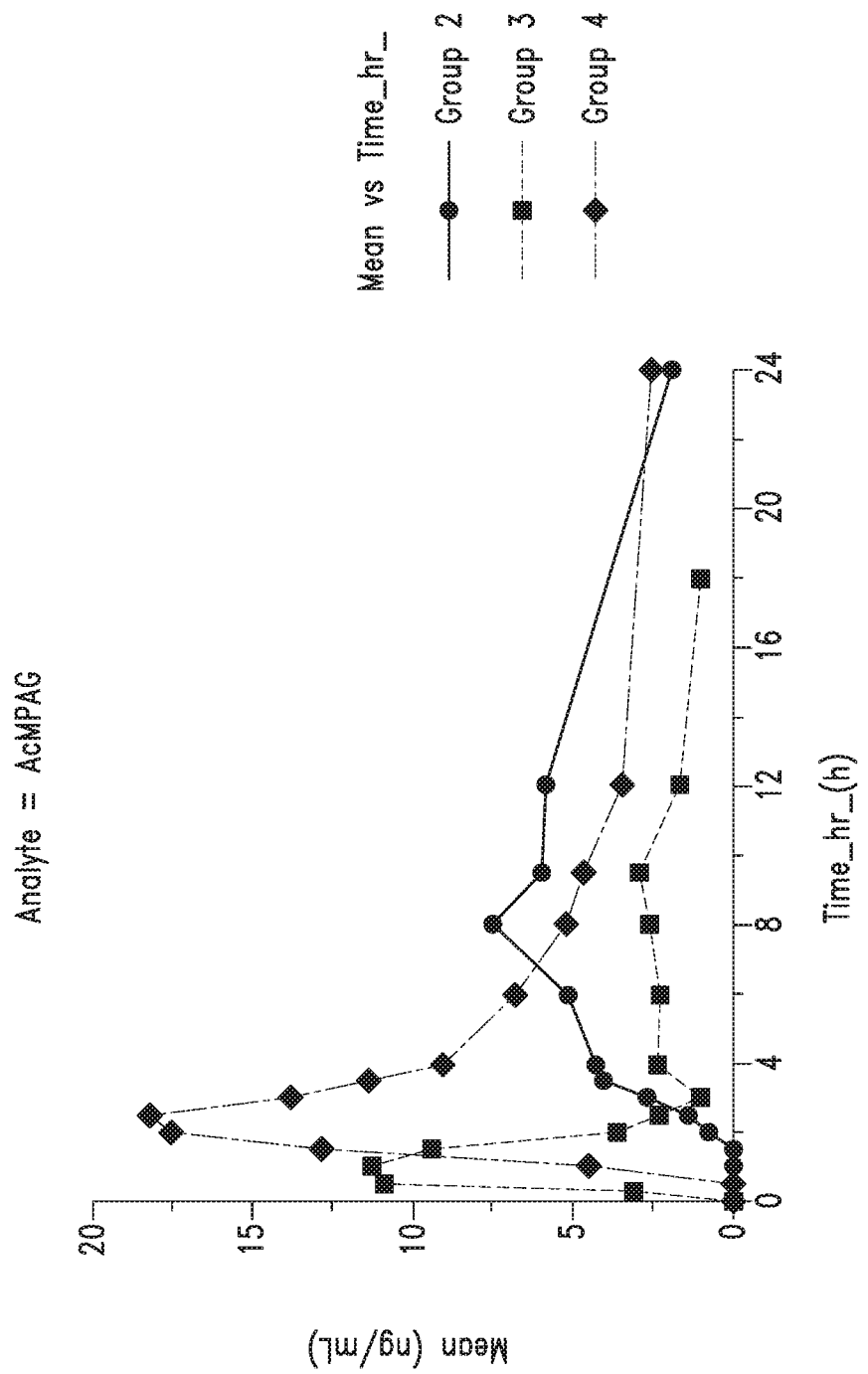
FIG. 12 shows mean serum levels (ng/mL) of the MPA metabolite acyl MPA glucoronide (AcMPAG) measured in the indicated canine treatment groups.
Figure 13:
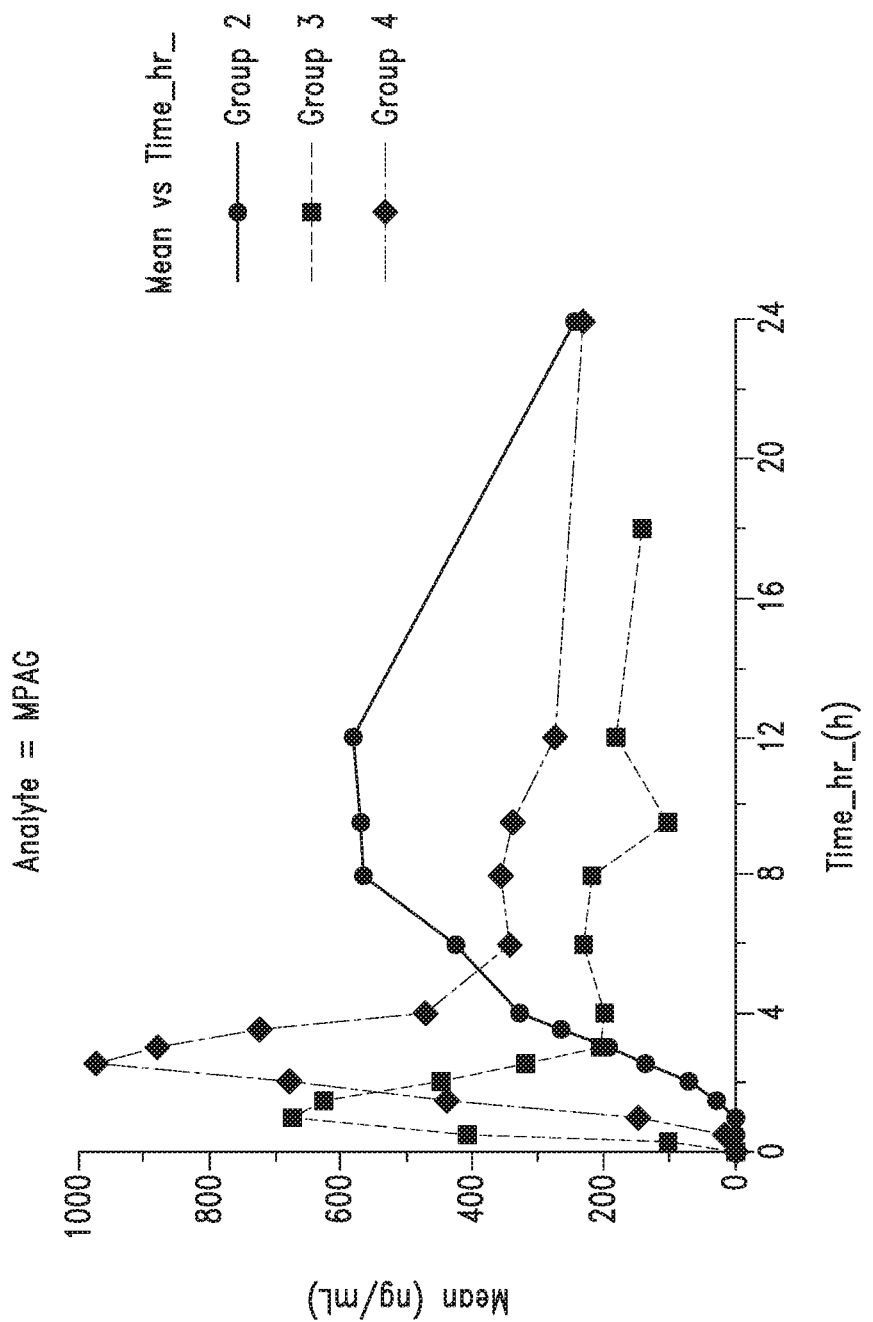
FIG. 13 shows mean serum levels (ng/mL) of the MPA metabolite MPA glucuronide (MPAG) measured in the indicated canine treatment groups.

FIG. 9 shows release of sodium mycophenolate from a modified release composition comprising a solvent-based coating. pH was switched from 1.2 to 6.8 following 2 h incubation.

Table 7 below provides MPA active agent release data from two exemplary compositions according to the present disclosure. Two sets of extended-release enteric-coating Na.MPA coated beads were prepared as described above (22 wt % Surelease coating and 30 wt % coating) and placed in acid (2 h, pH 1.2) followed by a buffer that raised pH to approximately 6.8.

TABLE 7

| Hours Following Administration | % NaMPA released (22% Surelease) | % NaMPA released (30% Surelease) |
|---|---|---|
| 0.5 | 0.9 | 0.0 |
| 1 | 3.2 | 1.5 |
| 2 | 7.9 | 4.9 |
| 2.5 | 25.1 | 13.2 |
| 3 | 35.8 | 21.4 |
| 4 | 51.3 | 31.7 |
| 5 | 61.4 | 40.7 |
| 6 | 67.9 | 48.0 |
| 7 | 72.8 | 54.0 |
| 8 | 76.2 | 59.1 |
| 10 | 81.5 | 66.1 |
| 14 | 86.9 | 76.1 |

Example 2

Preparation of Mycophenolate Modified Release Mini-Tablets

Materials

| | |
|---|---|
| Mycophenolate Sodium | 20-60%, suitably 50% |
| Microcrystalline cellulose | 30-60%, suitably 43% |
| Poly Vinyl pyrrolidone (PVP) | 1-10%, suitably 5% |
| Magnesium Stearate | 0.5-5%, suitably 2% |

The required quantities of mycophenolate sodium and microcrystalline cellulose were mixed together in a high shear mixer for about 5 minutes.

The required quantity of PVP was dissolved in water to form a 10% w/w solution of PVP.

The PVP solution was gradually added to the high shear mixer and the blend was mixed until a wet mass was formed.

The wet mass was transferred to a fluid bed dryer and dried.

The dried granulation was passed through a sieve such that very coarse and very fine particles were removed.

The sieved granulation was transferred to a V blender and mixed with the Magnesium stearate for about 3 minutes.

The lubricated granules were compressed into mini-tablets using a 2 mm round standard concave multi tip tooling on a compression press.

The mini-tablets were coated with a seal coat, a modified-release layer, and a protective layer, as described herein.

The appropriate quantity of mini-tablets can be administered to the veterinary subject, either filled in a capsule, as a slurry, as a sachet, a dragee, etc.

Example 3

In Vivo Pharmacokinetics of MPA in a Veterinary Model

Two single dose cross-over studies were conducted using a canine model (male beagle dogs) to evaluate the potential of an enteric coated-extended release sodium mycophenolate formulation ("EC-ER-Na.MP"). In a first cross-over study, the pharmacokinetics of MPA and its metabolites (MPAG and AcMPAG) following oral dosing of 180 mg of EC-Na.MPA was compared with intracolonic (IC) administration of Na.MPA. In a second cross-over study, 270 mg of an EC-ER-Na.MPA formulation was administered in the both fed and fasted states and pharmacokinetics were compared with oral administration of 10 mg/kg MMF in the fasted state. Both studies were conducted by Absorption Systems (San Diego, Calif.).

Study 1: For three days prior to IC dosing, dogs (n=5) were offered a soft diet consisting of canned wet food (Pedigree® Choice Cuts). Otherwise, the dogs were offered their standard diet (LabDiet 5006 laboratory canine diet). Prior to each dosing event, the dogs were fasted for 12 hours prior to dosing until 4 hours post-dose, when food was returned. Animals had free access to water throughout the study. Prior to IC dosing, each dog was given a non-stimulant enema approximately 1 hour prior to dosing to remove feces from the colon. Prior to PO dosing, each dog (n=5) was pre-treated with an intramuscular dose of pentagastrin (6 μg/kg) approximately 30 minutes prior to dosing. Capsules were administered by placement in the back of the throat followed by a 10 mL flush with water.

Each dog received a total dose of 180 mg of MPA for each dose. For IC dosing, MPA was delivered as a solution via an endoscope, and for PO dosing each dog received a single Myfortic® 180 mg enteric coated capsule. Following administration, blood samples were collected up to 24 hours post-dose. Plasma concentrations of MPA, MPAG, and AcMPAG were determined with a qualified LC-MS/MS method, and pharmacokinetic parameters were determined with WinNonlin v.6.4 software.

Following IC dosing of MPA, maximum plasma concentrations (average $C_{max}$ of 29460±12587 ng/mL) were observed between 5 and 30 minutes post-dose. The average half-life was 5.55±1.77 hours, and the average exposure based on the dose-normalized $AUC_{last}$ was 1817±925 hr*kg*ng/mL/mg. MPAG after MPA dosing had an average $C_{max}$ of 4826±1156 ng/mL. The $t_{max}$ for MPAG ranged from 15 minutes to 1 hour post-dose, and the average $AUC_{last}$ was 11702±4794 hr*ng/mL. AcMPAG after MPA dosing had an average $C_{max}$ of 303±87.8 ng/mL. The $t_{max}$ for MPAG ranged from 5 to 15 minutes post-dose, and the average $AUC_{last}$ was 233±160 hr*ng/mL.

Following PO dosing of MPA, maximum plasma concentrations (average $C_{max}$ of 27320±12037 ng/mL) were observed between 30 minutes and 2 hours post-dose. The average half-life, determined in 2 dogs, was 4.49 hours, and the average exposure based on the dose-normalized $AUC_{last}$ was 2234±799 hr*kg*ng/mL/mg. MPAG after MPA dosing had an average $C_{max}$ of 14316±5033 ng/mL. The $t_{max}$ for MPAG ranged from 1 to 2 hours post-dose, and the average AUClast was 28882±8313 hr*ng/mL. AcMPAG after MPA dosing had an average $C_{max}$ of 426±113 ng/mL. The $t_{max}$ for MPAG ranged from 30 minutes to 2 hours post-dose, and the average $AUC_{last}$ was 529±217 hr*ng/mL.

Based on average values, systemic exposure to MPA was similar following IC and PO dosing. The average $C_{max}$ after IC and PO doses were 29460 and 27320 ng/mL, respectively, and the average dose-normalized $AUC_{last}$ values were 1817 and 2234 hr*kg*ng/mL/mg, respectively. However, MPA did appear to be more rapidly absorbed following IC dosing in comparison to the PO dose. MPAG was present at a much higher concentration in the plasma than AcMPAG. Systemic exposure to each of these glucuronide metabolites after IC dosing was approximately 40% of that after PO dosing. The average $AUC_{last}$ for MPAG was 28882 hr*ng/mL after PO dosing and 11702 hr*ng/mL after IC dosing. The average $AUC_{last}$ for AcMPAG was 529 hr*ng/mL after PO dosing and 233 hr*ng/mL after IC dosing.

The mean pharmacokinetic parameters and the drug to metabolite ratios are summarized in Table 8. The MPA/MPAG ratio and MPA/AcMPAG ratio were each observed to be almost 2-fold higher following the IC dosing compared to the oral administration.

TABLE 8

Mean MPA, MPAG and AcMPAG Pharmacokinetic Parameters following Oral and Intracolonic Administration of Na•MPA (n = 5 male beagle dogs)

| | MPA | | MPAG | | AcMPAG | | MPA/MPAG | MPA/AcMPAG |
|---|---|---|---|---|---|---|---|---|
| | Mean | SD | Mean | SD | Mean | SD | Ratio | Ratio |
| ORAL | | | | | | | | |
| Animal Weight (kg) | 11.1 | 0.5 | | | | | | |
| Dosed per dog (mg) | 180 | 0 | | | | | | |
| Dose (mg/kg) | 16.2 | 0.7 | | | | | | |
| $C_{max}$ (ng/mL) | 27320 | 12037 | 14316 | 5033 | 426 | 113 | | |
| $t_{max}$ (hr) | 1 | 0.61 | 1.4 | 0.55 | 1.1 | 0.55 | | |
| $t_{1/2}$ (hr) | 4.49 | ND | 7.12 | 1.95 | ND | ND | | |
| $MRT_{last}$ (hr) | 2.86 | 0.856 | 3.75 | 0.371 | 1.71 | 0.628 | | |
| $AUC_{last}$ (hr · ng/mL) | 36435 | 13501 | 28882 | 8313 | 529 | 217 | 1.42 | 88.40 |
| $AUC_\infty$ (hr · ng/mL) | 45693 | ND | 30360 | 9234 | ND | ND | 1.29 | ND |
| INTRACOLONIC | | | | | | | | |
| Animal Weight (kg) | 10.7 | 0.5 | | | | | | |
| Dosed per dog (mg) | 180 | 0 | | | | | | |
| Dose (mg/kg) | 16.8 | 0.8 | | | | | | |
| $C_{max}$ (ng/mL) | 29460 | 12587 | 4826 | 1156 | 303 | 87.8 | | |
| $t_{max}$ (hr) | 0.23 | 0.17 | 0.6 | 0.38 | 0.22 | 0.07 | | |
| $t_{1/2}$ (hr) | 5.55 | 1.77 | 6.61 | 2.36 | ND | ND | | |
| $MRT_{last}$ (hr) | 2.76 | 0.324 | 4.16 | 0.688 | 1.33 | 0.897 | | |
| $AUC_{last}$ (hr · ng/mL) | 30993 | 17092 | 11702 | 4794 | 233 | 160 | 2.86 | 171.19 |
| $AUC_\infty$ (hr · ng/mL) | 31948 | 17903 | 13475 | 4252 | ND | ND | 2.45 | ND |

$C_{max}$: maximum plasma concentration;
$t_{max}$: time of maximum plasma concentration;
$t_{1/2}$: half-life; $MRT_{last}$: mean residence time, calculated to the last observable time point;
$AUC_{last}$: areaunder the curve, calculated to the last observable time point;
$AUC_\infty$: area under the curve, extrapolated to infinity;
BLOQ: below the limit of quantitation (1 ng/mL);
ND: not determined.

Study 2: In this treatment cross-over study, the pharmacokinetics of MPA and its metabolites (MPAG and AcMPAG) following 270 mg EC-ER-Na.MP ("OKV-1001") administered in the fed and fasted state were compared with those following oral administration of immediate release 10 mg/kg MMF in a fasted state (n=5 per dose group; same group of dogs for each treatment).

For EC-ER-Na.MP and MMF administration in the fasted state, dogs were fed a certified laboratory diet (5006 laboratory canine diet from LabDiet) and then fasted for a minimum of twelve hours prior to dosing. Food was provided approximately 4 hours post-dose. Water was supplied ad libitum to the animals.

For EC-ER-Na.MP administration in the fed state, dogs were fed a certified laboratory diet (5006 laboratory canine diet from LabDiet), fasted for a minimum of twelve hours, and then fed (Alpo Can food) prior to dosing and then dosed no more than 30 minutes post completion of food. The amount of food provided and consumed by each animal was recorded. Regular lab diet was provided approximately 4 hours post-dose. Water was supplied ad libitum to the animals.

For MMF administration, an MMF oral suspension was prepared according to the instructions for Cellcept®. Leftover dosing solutions were stored at room temperature.

For both EC-ER-Na.MP treatments, blood was collected pre-dosing, then at either: 30 minutes, 1, 1.5, 2, 2.5, 3, 3.5, 4, 6, 8, 9, 12, and 24 hours (processed to obtain plasma); or 1, 2, 3, 4, 6, 8, 12, and 24 hours (processed to PBMC). For the MMF treatment, blood was collected at pre-dose, 15 minutes, 30 minutes, 1, 1.5, 2, 2.5, 3, 4, 6, 8, 9, 12, and 18 hours (processed to plasma); or at pre-dose, 1, 2, 3, 4, 6, 8, 12, and 18 hours (processed to obtain PBMCs).

Plasma concentrations of MPA, MPAG, and AcMPAG were determined with a qualified LC-MS/MS method, and pharmacokinetic parameters were determined with WinNonlin v.6.4 software. Plasma concentration curves are shown in FIGS. 10-13. The mean pharmacokinetic parameters and drug to metabolite ratios are summarized in Table 9. Under fasted conditions, the MPA/MPAG ratio was 1.5 to 2.0 fold higher with EC-ER-Na.MP compared to the reference oral dosing (Table 9). The MPA/AcMPAG ratio also trended to be higher, although to a lesser extent.

TABLE 9

Mean Pharmacokinetic Parameters of MPA and Metabolites Following Oral MMF and EC-ER-Na•MP Administration

|  | MPA | | MPAG | | AcMPAG | | MPA/MPAG | MPA/AcMPAG |
| --- | --- | --- | --- | --- | --- | --- | --- | --- |
|  | Mean | SD | Mean | SD | Mean | SD | Ratio | Ratio |
| ORAL MMF | | | | | | | | |
| Animal Weight (kg) | 11 | 1.4 | | | | | | |
| MMF Dose (mg/kg) | 10 | — | | | | | | |
| Dose (mg/kg) MPA Equivalent | 7.39 | — | | | | | | |
| $C_{max}$ (ng/mL) | 1991 | 1434.5 | 800.2 | 300.8 | 18.25 | 14.61 | | |
| $t_{max}$ (hr) | 0.75 | 0.5 | 1.1 | 0.42 | 0.75 | .05 | | |
| $t_{1/2}$ (hr) | 5.78 | 5.68 | 14.30 | 10.91 | 2.42 | 0.65 | | |
| $MRT_{last}$ (hr) | 5.89 | 1.19 | 7.2 | 0.65 | 5.83 | 0.44 | | |
| $AUC_{last}$ (hr? · ng/mL) | 5644 | 2144 | 3899 | 1240 | 44.6 | 21.7 | 1.48 | 139.8 |
| $AUC_?$ (hr? · mg/mL) | 6543 | 3277 | 6615.7 | 2637.8 | 50.8 | 23.7 | 1.02 | 133.3 |
| EC-ER-Na•MPA | | | | | | | | |
| Animal Weight (kg) | 11.1 | 1.3 | | | | | | |
| Na•MPA Dose (mg) | 270 | — | | | | | | |
| Dose (mg/kg) MPA Equivalent | 22.94 | 2.47 | | | | | | |
| $C_{max}$ (ng/mL) | 2334 | 823.6 | 983.8 | 364.9 | 20.98 | 8.63 | | |
| $t_{max}$ (hr) | 2.3 | 0.27 | 2.3 | 0.45 | 2.1 | 0.42 | | |
| $t_{1/2}$ (hr) | 7.53 | 0.45 | 8.73 | 1.29 | 6.62 | 2.62 | | |
| $MRT_{last}$ (hr) | 8.44 | 1.19 | 9.89 | 1.77 | 7.9 | 2.06 | | |
| $AUC_{last}$ (hr? · ng/mL) | 15187 | 2678 | 7884.5 | 2771 | 120.9 | 50.3 | 2.18 | 169.0 |
| $AUC_?$ (hr? · ng/mL) | 18140 | 3111 | 10784 | 5110 | 145.9 | 63.6 | 1.99 | 163.0 |

$C_{max}$: maximum plasma concentration;
$t_{max}$: time of maximum plasma concentration;
$t_{1/2}$: half-life calculated using 2 points in the terminal phase;
$MRT_{last}$: mean residence time, calculated to the last observable time point;
$AUC_{last}$: area under the curve, calculated to the last observable time point;
$AUC_?$: area under the curve, extrapolated to infinity, if $t_{1/2}$ value was not available mean group value was used;
BLOQ: below the limit of quantitation (1 ng/mL);
ND: not determined.

Figure 14:
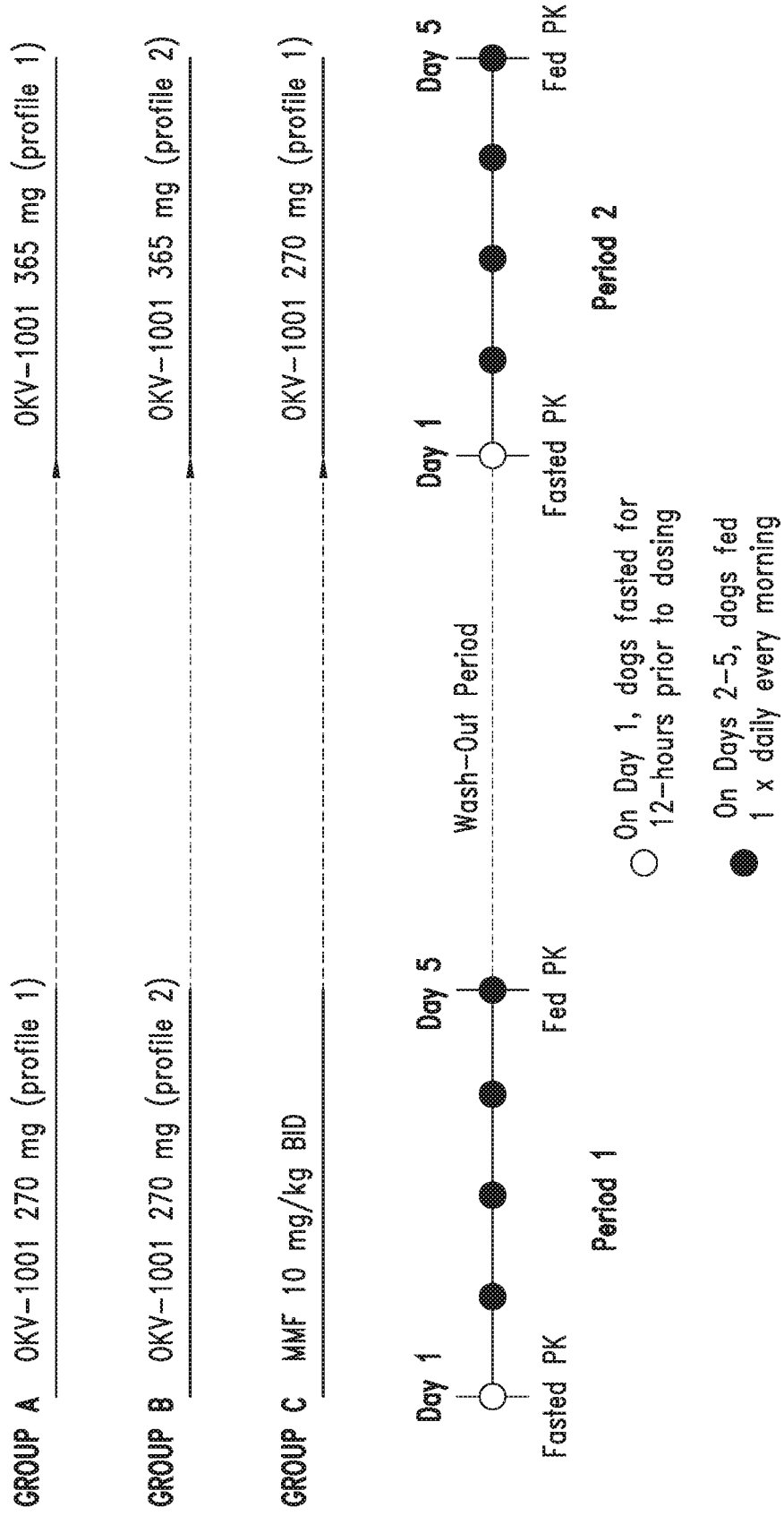
FIG. 14 provides a schematic diagram showing the design of a 2-treatment, 2-period, sequential adaptive cross-over study by the inventors of the present disclosure.

Study 3: Another cross-over study was performed to determine the single-dose and steady state pharmacokinetics of MPA and its metabolites (MPAG and AcMPAG). The study design is illustrated in FIG. 14. Specifically, three (3) groups of healthy male beagle dogs (n=7 per group for a total of 21 dogs; Marshall BioResources, North Rose, N.Y., USA) participated in a two-treatment, two-period, sequential, adaptive cross-over study. Two five-day, repeat-dosing study periods were separated by a 16-day washout period. Dogs were at least two years of age at the time of enrollment.

In the first five-day period, three groups of dogs (n=7 per group) were randomized to receive either OKV-1001 (270 mg) Profile 1 QD (Group A), OKV-1001 (270 mg) Profile 2 QD (Group B) or MMF (10 mg/kg) oral suspension BID (Group C). Profile 1 was formulated for faster release of the MPA active agent as compared to Profile 2. MMF oral suspension (CellCept® oral suspension, Genentech USA Inc., South San Francisco, Calif.) dosed at 10 mg/kg B.I.D served as the reference group. A 16-day wash period ensued after the first five-day period, and results from the first period were examined. Dogs were then crossed-over in the second period to receive OKV-1001 (365 mg) Profile 1 QD (Group A) or OKV-1001 (365 mg) Profile 2 QD (Group B) or either OKV-1001 (270 mg) Profile 1 QD (Group C). The treatments received by the dogs in each group and period are summarized in Table 10.

TABLE 10

Treatments Received by Each Group in Study 3

| | Period 1 | Period 2 |
|---|---|---|
| Group A (n = 7) | OKV-1001$_{P1}$ 270 mg (QD) | OKV-1001$_{P1}$ 365 mg (QD) |
| Group B (n = 7) | OKV-1001$_{P2}$ 270 mg (QD) | OKV-1001$_{P2}$ 365 mg (QD) |
| Group C (n = 7) | MMF 10 mg/kg (BID) | OKV-1001$_{P1}$ 270 mg (QD) |

The two study periods had identical feeding and sampling procedures. On Day 1, PK samples were collected after a 12-hour fast, while samples were collected 1 hour after the animals were fed on Day 5. At the time of dosing, any uneaten food was removed, and the amount of food provided and consumed by each animal was recorded. On Days 2-5, animals were fed once daily in the morning, 1 hour prior to administration of the morning dose.

On Day 1 and Day 5, serial blood samples collected via the jugular vein were collected prior to dosing (0 min) and at 15 and 30 min, and then 1, 1.5, 2, 2.5, 3, 4, 6, 8, 9 and 12 hours after MMF administration. For OKV-1001, samples were collected prior to dosing (0 min), and at 30 min, and then 1, 1.5, 2, 2.5, 3, 3.5, 4, 6, 8, 9, 12 and 24 hours. A qualified and validated GLP ready LC-MS/MS method was used to quantify plasma MPA, MPAG, AcMPAG plasma concentrations.

The general health of each animal was assessed at every blood sampling time point during the course of the study. On study days with no blood sampling or only one blood sampling time point, the general health was assessed at least twice daily (AM and PM).

Figure 15:
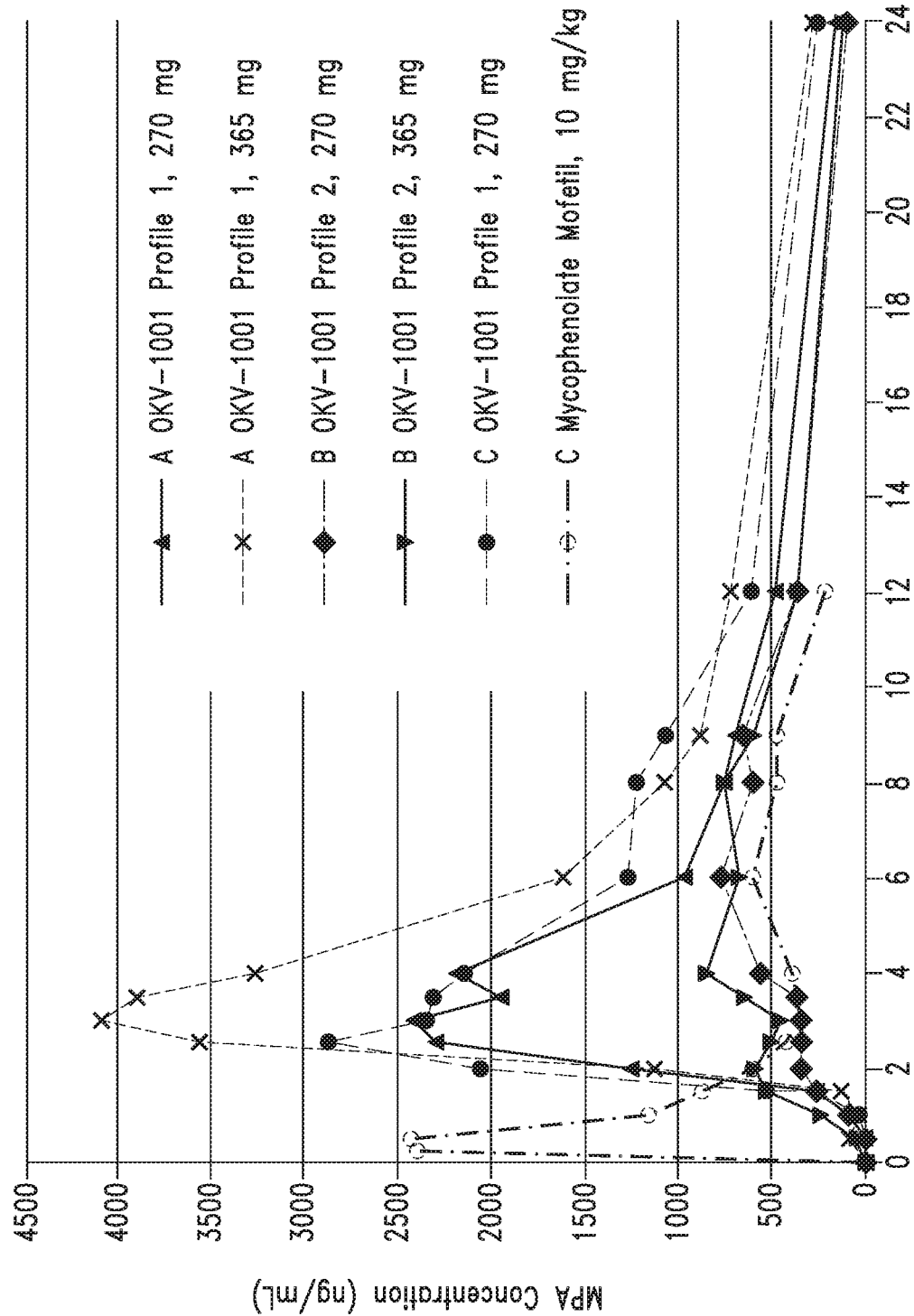
FIG. 15 shows Day 1 serum MPA concentrations over time from the canine "Period 1" and "Period 2" treatment groups depicted in FIG. 14.
Figure 16:
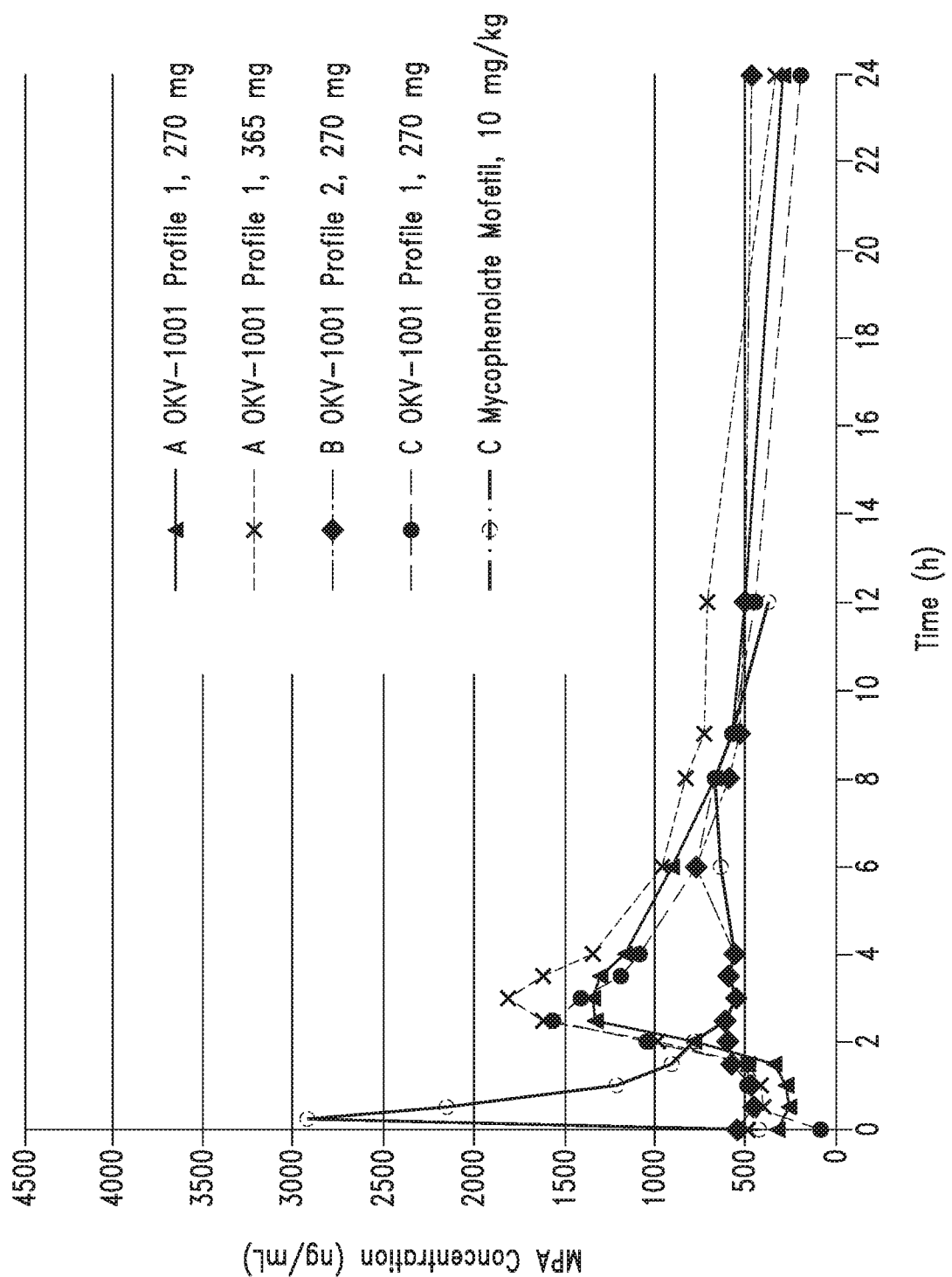
FIG. 16 shows Day 5 serum MPA concentrations over time from the canine "Period 1" and "Period 2" treatment groups depicted in FIG. 14.

Standard non compartmental pharmacokinetic parameters ($C_{max}$, $T_{max}$, $t_{1/2}$, $AUC_{last}$ and $AUC_{inf}$ following the Day 1 dosing; $C_{max}$, $T_{max}$, and $AUC_{tau}$ following the Day 5 dosing where tau is 12 h for MMF and 24 h for OKV-1001) were estimated using Phoenix Winnonlin software 64 (Build 7.0.0.2535) for MPA, MPAG and AcMPAG. MPA plasma concentration levels for each treatment group on Day 1 (fasted; single-dose) are shown in FIG. 15. MPA plasma concentration levels for each treatment group on Day 5 (fed; steady state) are shown in FIG. 16. Calculated drug:metabolite (D:M) ratios for Group C, Group A, and Group B are shown in Tables 11, 12, and 13, respectively. Reference ratio values from Study 2 are also shown. Non-compartmental PK parameter estimates for all treatment groups are provided in Table 14. It should be noted that data from Group B/Period 2/Day 5 was not obtained from 5 of the 7 dogs.

TABLE 11

Study 3 Group C and Study 2: Mean D:M Ratio Summary

| | Study 3 (Repeat Dose) | | Study 2 (Single Dose) | |
|---|---|---|---|---|
| | MMF | OKV-1001 (270 mg) | MMF | OKV-1001 (270 mg) |
| MPA/MPAG Day 1 | 1.6 (0.78-3.07) | 1.5 (0.69-2.36) | 1.02 (0.70-1.77) | 1.99 (1.10-3.30) |
| MPA/MPAG Day 5 | 1.6 (0.84-3.35) | 0.84 (0.48-1.43) | | |
| MPA/AcMPAG Day 1 | 130 (80-219) | 90 (65-160) | 133 (90-229) | 163 (94-380) |
| MPA/AcMPAG Day 5 | 84 (60-168) | 76 (53-145) | | |

TABLE 12

Study 3 Group A and Study 2: Mean D:M Ratio Summary

| | Study 3 (Repeat Dose) | | Study 2 (Single Dose) | |
|---|---|---|---|---|
| | OKV-1001 P1 (270 mg) | OKV-1001 P1 (365 mg) | MMF | OKV-1001 (270 mg) |
| MPA/MPAG Day 1 | 1.97 (1.05-4.73) | 1.48 (0.80-3.18) | 1.02 (0.70-1.77) | 1.99 (1.10-3.30) |
| MPA/MPAG Day 5 | 1.27 (0.81-2.71) | 0.75 (0.42-1.52) | | |
| MPA/AcMPAG Day 1 | 119 (77-155) | 94 (81-130) | 133 (90-229) | 163 (94-380) |
| MPA/AcMPAG Day 5 | 104 (47-191) | 74 (51-128) | | |

TABLE 13

Study 3 Group B and Study 2: Mean D:M Ratio Summary

| | Study 3 (Repeat Dose) | | Study 2 (Single Dose) | |
|---|---|---|---|---|
| | OKV-1001 P2 (270 mg) | OKV-1001 P2 (365 mg) | MMF | OKV-1001 (270 mg) |
| MPA/MPAG Day 1 | 1.95 (1.22-3.5) | 1.10 (1.0-1.94) | 1.02 (0.70-1.77) | 1.99 (1.10-3.30) |
| MPA/MPAG Day 5 | 1.6 (0.86-2.96) | 0.6 (0.52, 0.70) (n = 2) | | |
| MPA/AcMPAG Day 1 | 163.5 (91-418) | 131 (92-273) | 133 (90-229) | 163 (94-380) |
| MPA/AcMPAG Day 5 | 145 (63-257) | 80 (69, 91) (n = 2) | | |

TABLE 14

Mean Single-Dose and Steady State MPA and MPAG Pharmacokinetic Parameters - Group A (n = 7)

| Period/Formulation Group A | Day | | Tmax hr | Cmax ng/mL MPA | AUC$^a$ hr*ng/mL | Tmax hr | Cmax ng/mL MPAG | AUC$^a$ hr*ng/mL |
|---|---|---|---|---|---|---|---|---|
| | | | | Group A | | | | |
| Period 1/ OKV-1001 Profile 1, 270 mg | 1 | Mean | 3.00 | 2897.1 | 18078 | 3.07 | 953.6 | 9873 |
| | | SD | 0.87 | 1283.8 | 7615 | 0.53 | 146.0 | 2721 |
| | 5 | Mean | 2.93 | 1515.9 | 14093 | 3.36 | 1640.4 | 12182 |
| | | SD | 0.45 | 535.8 | 6429 | 0.38 | 704.6 | 5999 |
| Period 2/ OKV-1001 Profile 1, 365 mg | 1 | Mean | 3.00 | 4895.7 | 28200$^b$ | 3.64 | 2311.4 | 20426$^c$ |
| | | SD | 0.58 | 987.9 | 11231 | 0.48 | 732.9 | 5572 |
| | 5 | Mean | 2.93 | 1920.3 | 17464 | 3.29 | 3442.9 | 24234 |
| | | SD | 0.35 | 924.8 | 9670 | 0.49 | 877.4 | 10902 |
| | | | | Group B$^d$ | | | | |
| Period 1/ OKV-1001 Profile 2, 270 mg | 1 | Mean | 7.14 | 835.1 | 9503 | 7.57 | 310.6 | 4957 |
| | | SD | 1.46 | 463.8 | 4215 | 1.51 | 65.7 | 1357 |
| | 5 | Mean | 5.14 | 854.0 | 12981 | 6.57 | 505.9 | 6899 |
| | | SD | 2.78 | 861.7 | 15691 | 7.86 | 309.2 | 4649 |
| Period 2/ OKV-1001 Profile 2, 365 mg | 1 | Mean | 4.21 | 1037.3 | 11099 | 7.29 | 714.4 | 9747 |
| | | SD | 1.82 | 654.8 | 7237 | 1.98 | 169.4 | 2496 |
| | | | | Group C | | | | |
| Period 1/ Mycophenolate Mofetil 10 mg/kg | 1 | Mean | 0.32 | 2950.0 | 8231 | 0.43 | 1032.1 | 5303 |
| | | SD | 0.12 | 1730.4 | 3412 | 0.12 | 368.0 | 1497 |
| | 5 | Mean | 0.36 | 3238.6 | 8672 | 0.71 | 1430.6 | 5962 |
| | | SD | 0.13 | 1437.8 | 2939 | 0.27 | 722.7 | 1687 |
| Period 2/ OKV-1001 Profile 1, 270 mg | 1 | Mean | 2.79 | 3042.9 | 23324 | 3.50 | 1584.3 | 16749$^b$ |
| | | SD | 0.70 | 612.9 | 10366 | 1.22 | 333.0 | 7447 |
| | 5 | Mean | 2.79 | 1666.1 | 13023 | 3.00 | 2382.9 | 15814 |
| | | SD | 0.39 | 721.3 | 4738 | 0.50 | 547.7 | 3758 |

$^a$AUC$_{inf}$ for Day 1 and AUC$_{0-24}$ for Day 5
$^b$n = 6
$^c$n = 5
$^d$Group B/Period 2/Day 5 is not presented because data are not available from 5 dogs.

It will be readily apparent to one of ordinary skill in the relevant arts that other suitable modifications and adaptations to the methods and applications described herein can be made without departing from the scope of any of the embodiments. Further, it is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application Ser. No. 62/470,806, and U.S. Provisional Patent Application Ser. No. 62/503,270, are incorporated herein by reference, in their entirety. Aspects of the embodiments can be modified, if necessary to employ concepts of the various patents, applications and publications to provide yet further embodiments.

All publications, patents and patent applications mentioned in this specification are herein incorporated by reference to the same extent as if each individual publication, patent or patent application was specifically and individually indicated to be incorporated by reference.

What is claimed is:

1. A method for delivering a sodium mycophenolate composition to a dog, comprising delivering a plurality of modified-release compositions to a lower gastrointestinal tract of the dog via oral administration, wherein the modified-release compositions comprise:
   i. a core having a diameter from about 0.5 mm to about 3 mm;
   ii. a sodium mycophenolate layer disposed over at least a portion of the core;
   iii. a seal coat disposed over the sodium mycophenolate layer;
   iv. a modified-release layer disposed over the seal coat layer; and
   v. a protective layer disposed over the modified-release layer,
   wherein the modified-release layer comprises ethyl cellulose from about 15 wt % to about 35 wt % of the composition, the protective layer comprises a methacrylate-based polymer from about 8 wt % to about 15 wt % of the composition and does not dissolve at a pH below 6.0, the sodium mycophenolate is from about 20 wt % to about 90 wt % of the composition, and the sodium mycophenolate is released in the dog according to the following schedule:

| Hours Following Administration | % Sodium Mycophenolate Released |
| --- | --- |
| 0.5 | about 0.0 to about 1.0 |
| 2 | about 3.0 to about 10.0 |
| 2.5 | about 10.0 to about 30.0 |
| 3 | about 15.0 to about 40.0 |
| 4 | about 25.0 to about 55.0 |
| 6 | about 40.0 to about 75.0 |
| 7 | about 50.0 to about 80.0 |
| 10 | about 60.0 to about 90.0 |
| 14 | about 70.0 to about 100. |

2. The method according to claim 1, wherein the seal coat comprises a cellulose polymer, a poly(vinyl alchol), a hydroxypropyl methylcellulose polymer, a methylcellulose polymer, a hydroxyethylcellulose polymer, or any combination thereof.

3. The method according to claim 1, whereupon following the administration, the dog has MPA:metabolite ratio that is elevated as compared to a corresponding MPA:metabolite ratio obtained from a reference dog following administration of a reference immediate-release oral dosage of mycophenolate mofetil thereto.

4. The method according to claim 3, wherein the metabolite comprises MPAG, AcMPAG, or both.

5. The method according to claim 4, wherein the metabolite comprises MPAG and the MPA:MPAG ratio is from about 1:1 to about 10:1.

6. The method according to claim 4, wherein the metabolite comprises MPAG and the MPA:MPAG ratio is about 2:1.

7. The method according to claim 4, wherein the metabolite comprises AcMPAG and the MPA:AcMPAG ratio is from about 50:1 to 250:1.

8. The method according to claim 4, wherein the metabolite comprises AcMPAG and the MPA:AcMPAG ratio is about 150:1.

9. The method according to claim 1, wherein following the administration, the dog delivered the modified-release composition has a MPA $C_{max}$ of less than about 2500 ng/mL, less than about 2000 ng/mL, or less than about 1500 ng/mL.

10. The method according to claim 1, wherein the dog maintains a plasma MPA of more than about 500 ng/mL for at least about 3 hours, at least about 4 hours, or at least about 5 hours following $T_{max}$.

11. The method according to claim 1, wherein the dog has an autoimmune disease or disorder, a blood disorder associated with IMPDH activity, or is having, is about to have, or has recently had a transplant or graft procedure, or any combination thereof.

12. The method according to claim 1, wherein following the administration, the dog delivered the modified-release composition has a MPA $C_{max}$ of less than about 2500 ng/mL, less than about 2000 ng/mL, or less than about 1500 ng/mL; and the dog maintains a plasma MPA of more than about 500 ng/mL for at least about 3 hours, at least about 4 hours, or at least about 5 hours following $T_{max}$.

* * * * *